(12) United States Patent
Yonezu et al.

(10) Patent No.: US 9,335,311 B2
(45) Date of Patent: May 10, 2016

(54) GAS SENSOR

(71) Applicant: NGK SPARK PLUG CO., LTD., Nagoya-shi, Aichi (JP)

(72) Inventors: Kunihiko Yonezu, Mie-ken (JP); Norimasa Osawa, Inuyama (JP); Hisaharu Nishio, Tokai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 294 days.

(21) Appl. No.: 13/944,273

(22) Filed: Jul. 17, 2013

(65) Prior Publication Data

US 2014/0020446 A1    Jan. 23, 2014

(30) Foreign Application Priority Data

Jul. 19, 2012   (JP) ................................ 2012-160436
Apr. 23, 2013   (JP) ................................ 2013-090089

(51) Int. Cl.
  *G01N 7/00*    (2006.01)
  *G01N 33/00*   (2006.01)
  *G01N 27/406*  (2006.01)

(52) U.S. Cl.
  CPC ........ *G01N 33/0009* (2013.01); *G01N 27/4062* (2013.01)

(58) Field of Classification Search
  CPC .................................................... G01N 33/00

USPC ............ 73/23.2, 23.31, 31.05; 204/424, 426, 204/428, 431

See application file for complete search history.

(56) References Cited

U.S. PATENT DOCUMENTS

| 7,921,692 B2 * | 4/2011 | Isomura et al. .............. 73/23.31 |
| 2006/0101900 A1 * | 5/2006 | Nishio et al. ................. 73/31.05 |
| 2011/0174617 A1 * | 7/2011 | Tsuzuki et al. .............. 204/431 |
| 2011/0259084 A1 * | 10/2011 | Atsumi et al. ............... 73/31.05 |

FOREIGN PATENT DOCUMENTS

JP   2011-145270 A   7/2011

* cited by examiner

Primary Examiner — Hezron E Williams
Assistant Examiner — Hoang Nguyen
(74) Attorney, Agent, or Firm — Sughrue Mion, PLLC

(57) ABSTRACT

A gas sensor (200) in which individual ones of connection terminals (30) have, at a rear end portion, a first connection portion (31) connected to a corresponding connector terminal (60). Individual ones of the connector terminals have, at an end portion on a side toward separator (40), a second connection portion (61) connected to the first connection portion. One of the first and second connection portions assumes the form of an insertion piece (61g), and the other assumes the form of a female portion (31g) into which the insertion piece is inserted. At least one of the insertion piece and the female portion has an elastic portion (31a). The insertion piece is fitted into the female portion, and the elastic portion thereby elastically bends, whereby the first and second connection portions are elastically connected.

18 Claims, 17 Drawing Sheets

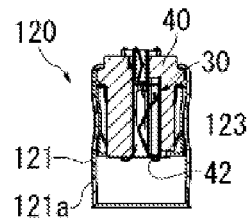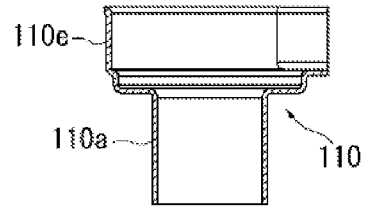
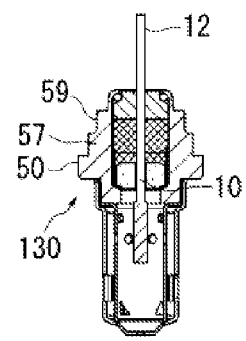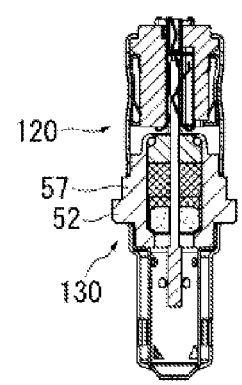
FIG. 6(a)  FIG. 6(b)
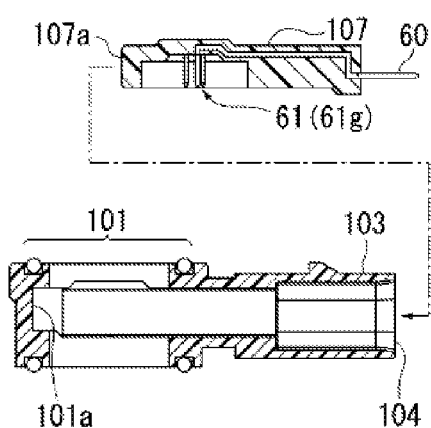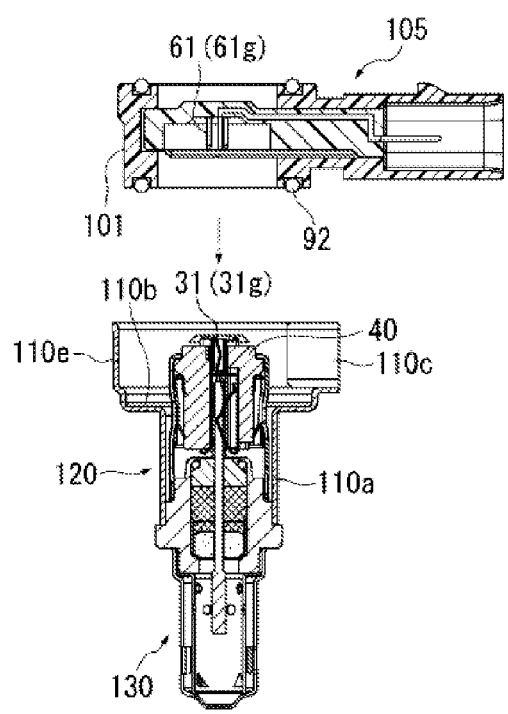
FIG. 6(c)  FIG. 6(d)

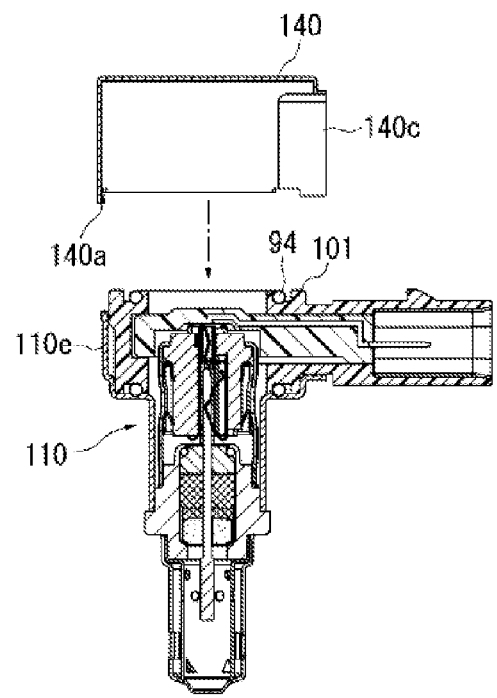
FIG. 7(e)
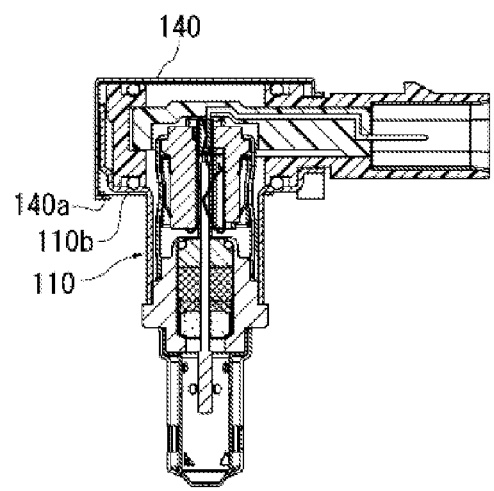
FIG. 7(f)
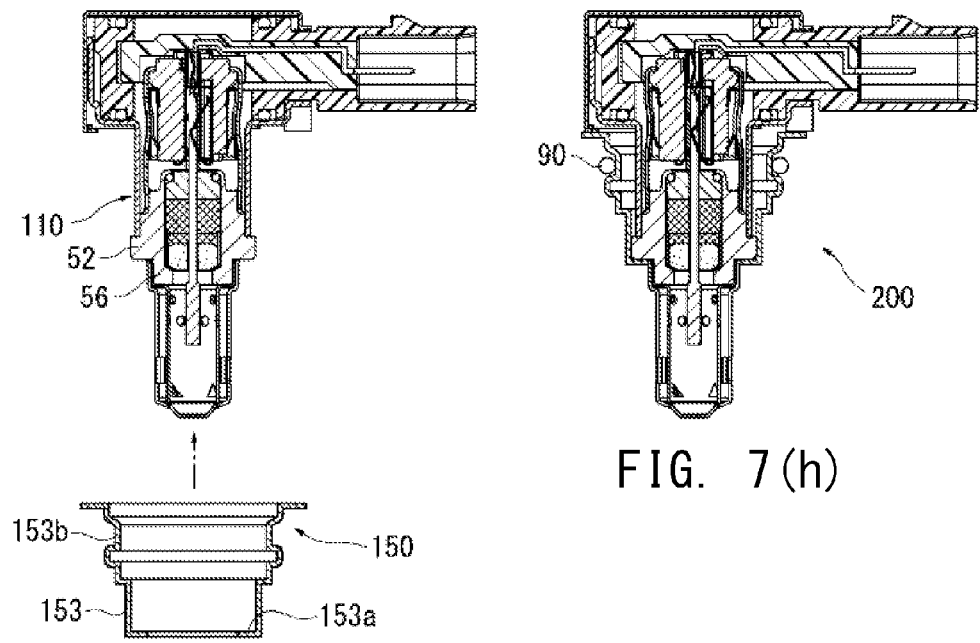
FIG. 7(g)
FIG. 7(h)

GAS SENSOR

BACKGROUND OF THE INVENTION

1. Field of the Invention

The present invention relates to a gas sensor having a gas sensor element for detecting the concentration of a particular gas.

2. Description of the Related Art

A gas sensor is mounted onto an intake system (e.g., an intake pipe or an intake manifold) or an exhaust system of an internal combustion engine, such as a diesel engine or a gasoline engine, for controlling, for example, combustion conditions by monitoring the concentration of a particular gas. A gas sensor generally used for performing such control is fixed by providing an externally threaded portion on the outside of a case (metallic shell) adapted to accommodate a gas sensor element therein, and is threadingly engaged with an internally threaded portion provided in a wall of the intake or exhaust system.

Meanwhile, in order to improve safety in the event of collision of a vehicle having an internal combustion engine, a clearance must be provided between the hood and engine parts; thus, the length of outward projection of the gas sensor from the intake system must be shortened. However, the gas sensor mentioned above has a limitation in shortening the length of outward projection of the gas sensor from the intake system. This is because connection terminals and lead wires for leading out detection outputs from the gas sensor element are extended rearward from the gas sensor.

Under these circumstances, a so-called lateral-lead-out-type gas sensor is known, as described in Patent Document 1, having a connector portion which extends, in a direction intersecting the axial direction, from a separator disposed on the rear side of the gas sensor element and to which detection outputs from the gas sensor element are led. According to this gas sensor, the axial height of the gas sensor is lowered, thereby shortening the length of projection of the gas sensor from the intake system when mounted to the intake system.

[Patent Document 1] Japanese Patent Application Laid-Open (kokai) No. 2011-145270

3. Problems to be Solved by the Invention

The lateral-lead-out-type gas sensor described in Patent Document 1 has a separator equipped with connection terminals disposed on the rear side of the gas sensor element, and allows for detection outputs to be led out from the connection terminals. A laterally extending lead frame is welded to the rear ends of the connection terminals; furthermore, the lead frame is welded to connector terminals extending from the connector portion. Thus, the lateral-lead-out gas sensor gives rise to problems of deterioration in production efficiency resulting from an increase in the number of welds, and an increase in the number of components resulting from use of the lead frame. Meanwhile, since the gas sensor element assumes a high temperature as a result of heating by its own heater and exposure to, for example, exhaust gas, the connection terminals connected to the gas sensor element are preferably formed of a heat resisting metal. By contrast, since the connector terminals are required to have low internal resistance for high electrical conductivity, generally, the connector terminals are preferably formed of a copper-based material. In the case where the materials of the connection terminals and the connector terminals differ, difficulty may be encountered in welding these terminals.

SUMMARY OF THE INVENTION

Thus, an object of the present invention is to provide a gas sensor in which the connection terminals connected to the gas sensor element and the corresponding connector terminals held in the connector portion are connected without welding, thereby improving productivity and reducing the number of components.

The above object has been achieved by providing (1) a gas sensor comprising: a gas sensor element extending in a direction of an axis, having a detection portion provided at a forward end thereof for detecting a particular gas component in a gas to be measured, and having an electrode pad provided at a rear end portion thereof; a metallic shell surrounding a radial circumference of the gas sensor element and holding the gas sensor element therein; an electrically insulating separator having a rear end portion of the gas sensor element disposed within an insertion hole thereof; a connection terminal which is inserted into the insertion hole and whose forward portion extends in the direction of the axis and is electrically connected to the electrode pad; a trunk member having a body portion surrounding the separator, and a connector portion extending from the body portion in a radial direction intersecting the direction of the axis and allowing an external device to be inserted thereinto and removed therefrom; and a connector terminal held in the connector portion and extending through the connector portion in a radial direction intersecting the direction of the axis. In the gas sensor, the connection terminal has, at a rear end portion, a first connection portion electrically connected to the connector terminal, and the connector terminal has, at an end portion on a side toward the separator, a second connection portion electrically connected to the first connection portion; one or both of the first connection portion and the second connection portion is bent such that the first connection portion and the second connection portion are juxtaposed with each other; one of the first connection portion and the second connection portion assumes the form of an insertion piece, the other one assumes the form of a female portion into which the insertion piece is inserted, and at least one of the insertion piece and the female portion has an elastic portion elastically bendable in a direction intersecting a direction of juxtaposition of the first connection portion and the second connection portion; and the insertion piece is fitted into the female portion such that the elastic portion elastically bends in the intersecting direction, whereby the first connection portion and the second connection portion are elastically connected.

According to the gas sensor (1), the insertion piece is fitted into the female portion, and the elastic portion thereby elastically bends in the intersecting direction, whereby the first connection portion and the second connection portion are elastically connected. Thus, detection outputs from the gas sensor element can be led out to the connector terminal via the connection terminal. Therefore, in the lateral-lead-out-type gas sensor, the connection terminals and the connector terminals can be electrically connected without welding, and productivity can thereby be improved. Also, a lead frame for welding the connection terminals and the connector terminals becomes unnecessary, and the number of components is thereby reduced.

Meanwhile, one of the first connection portion and the second connection portion may be bent such that the first and second connection portions are juxtaposed with each other, or both of the first connection portion and the second connection portion may be bent such that the first and second connection portions are juxtaposed with each other. In this case, the first connection portion and the second connection portion may or may not be juxtaposed in parallel with each other.

Also, the elastic portion may be provided at one or both of the insertion piece and the female portion. Furthermore, the invention is not limited to a single elastic portion, and a plurality of the elastic portions may be provided.

In a preferred embodiment (2) of the gas sensor (1) above, the second connection portion assumes the form of the insertion piece, and the first connection portion assumes the form of the female portion.

According to the gas sensor (2), the first connection portion is fixed to the separator, and the second connection portion is fitted to the first connection portion, thereby connecting the first connection portion and the second connection portion. Thus, by virtue of the second connection portion assuming the form of the insertion piece, the second connection portion does not come into contact with the separator, whereby chipping of the separator can be prevented.

In another preferred embodiment (3) of the gas sensor (2) above, the second connection portion is bent; the insertion piece extends in the direction of the axis; and the female portion of the first connection portion is located within the insertion hole.

According to the gas sensor (3), the female portion of the first connection portion is fixed in the insertion hole extending in the direction of the axis, and the insertion piece of the second connection portion is inserted into the female portion; therefore, insertion (fitting) is facilitated and ensured.

In a second aspect (4), the invention provides a gas sensor comprising a gas sensor element extending in a direction of an axis, having a detection portion provided at a forward end thereof for detecting a particular gas component in a gas to be measured, and having an electrode pad provided at a rear end portion thereof; a metallic shell surrounding a radial circumference of the gas sensor element and holding the gas sensor element therein; an electrically insulating separator having a rear end portion of the gas sensor element disposed within an insertion hole thereof; a connection terminal which is inserted into the insertion hole and extends in the direction of the axis and whose forward portion is electrically connected to the electrode pad; a trunk member formed of an electrically insulating material, having a body portion surrounding the separator, and a connector portion extending from the body portion in a direction intersecting the direction of the axis and allowing an external device to be inserted thereinto and removed therefrom; and a connector terminal held in the connector portion and extending through the connector portion in a direction intersecting the direction of the axis. In the gas sensor, the connection terminal has, at a rear end portion, a first connection portion electrically connected to the connector terminal, and the connector terminal has, at an end portion on a side toward the separator, a second connection portion electrically connected to the first connection portion; one or both of the first connection portion and the second connection portion is bent such that the first connection portion and the second connection portion are juxtaposed with each other; at least one of the first connection portion and the second connection portion has an elastic portion elastically bendable in a direction intersecting a direction of extension of the first connection portion and the second connection portion; and one connection portion of the first and second connection portions is sandwiched between a surface of the separator or an inner surface of the trunk member and the other connection portion such that the elastic portion elastically bends in the intersecting direction, whereby the first connection portion and the second connection portion are elastically connected.

According to the gas sensor (4), one connection portion is held between the other connection portion and the surface of the separator or the inner surface of the trunk member, and the elastic portion thereby elastically bends in the intersecting direction, whereby the first connection portion and the second connection portion are elastically connected. Thus, detection outputs from the gas sensor element can be led out to the connector terminal via the connection terminal. Therefore, in the lateral-lead-out-type gas sensor, the connection terminals and the connector terminals can be electrically connected without welding, and productivity can thereby be improved. Also, a lead frame for welding the connection terminals and the connector terminals becomes unnecessary, and the number of components is thereby reduced.

Meanwhile, one of the first connection portion and the second connection portion may be bent such that the first and second connection portions are juxtaposed with each other, or both of the first connection portion and the second connection portion may be bent such that the first and second connection portions are juxtaposed with each other. In this case, the first connection portion and the second connection portion may be or may not be juxtaposed in parallel with each other.

Also, the elastic portion may be provided at one or both of the first and second connection portions. Furthermore, the invention is not limited to a single elastic portion, and a plurality of the elastic portions may be provided.

In a preferred embodiment (5) of the gas sensor (4) above, the second connection portion is the one connection portion, and the first connection portion is the other connection portion.

According to the gas sensor (5), the first connection portion is fixed to the separator, and the second connection portion is fitted to the first connection portion, thereby connecting the first connection portion and the second connection portion. Thus, as a result of the second connection portion being the one connection portion, the surface of the separator or the inner surface of the trunk member and the first connection portion ensure connection of the second connection portion.

In a preferred embodiment (6) of the gas sensor (5) above, the second connection portion is bent and extends in the direction of the axis, and the second connection portion is disposed between an inner surface of the insertion hole of the separator and the first connection portion.

According to the gas sensor (6), the other connection portion; i.e., the first connection portion, is fixed in the insertion hole extending in the direction of the axis, and the second connection portion is held therebetween This configuration can reliably hold the second connection portion with greater facility.

In a preferred embodiment (7) of the gas sensor of any of (1) to (6) above, the connection terminal is formed of a material having a heat resistance that is higher than that of a material used to form the connector terminal.

The connection terminal is connected to the gas sensor element which assumes a high temperature as a result of heating by its own heater and exposure to, for example, exhaust gas. Thus, as a result of the connection terminal being formed of a material having heat resistance higher than that of a material used to form the connector terminal, the heat resistance of the connection terminal is improved.

In a preferred embodiment of the gas sensor of any one of (1) to (7) above, the connector terminal is formed of a copper-based material, and the connection terminal is formed of stainless steel or an Ni-based alloy.

In a preferred embodiment of the gas sensor of any one of (1) to (8) above, the trunk member further comprises an insulator which is accommodated in the body portion of the trunk member and in which a portion of the connector terminal is embedded.

Since a portion of the connector terminal is embedded in the insulator, the trunk member can be easily assembled by inserting, into the body portion, an assembly in which the connector terminal is held in the insulator.

In a preferred embodiment (10) of the gas sensor of any of (1) to (9) above, a plurality of the connection terminals are held in the separator. Even in a gas sensor having a plurality of the connection terminals, by means of the connection terminals being held in the separator, the configuration of the present invention can be easily attained.

In a preferred embodiment (11) of the gas sensor of any of (1) to (10) above, plural connector terminals are held in the trunk member. Even in a gas sensor having a plurality of the connector terminals, by means of the connector terminals being held in the separator, the configuration of the present invention can be easily attained.

In a preferred embodiment (12) of the gas sensor of any of (1) to (11) above, the elastic portion is a spring portion having a free end. By use of such a spring portion, the elastic force of the elastic portion is increased, whereby the first connection portion and the second connection portion are reliably connected.

Effect of the Invention

According to the present invention, the connection terminals connected to the gas sensor element and the corresponding connector terminals held in the connector portion are connected without welding, whereby productivity can be improved, and the number of components can be reduced.

BRIEF DESCRIPTION OF THE DRAWINGS

FIGS. 6(a)-6(d) are a set of process drawings showing an example method of manufacturing the gas sensor according to the first embodiment of the present invention.
FIGS. 7(e)-7(h) are a set of process drawings subsequent to FIGS. 6(a)-6(d).

DESCRIPTION OF REFERENCE NUMERALS

Figure 1:
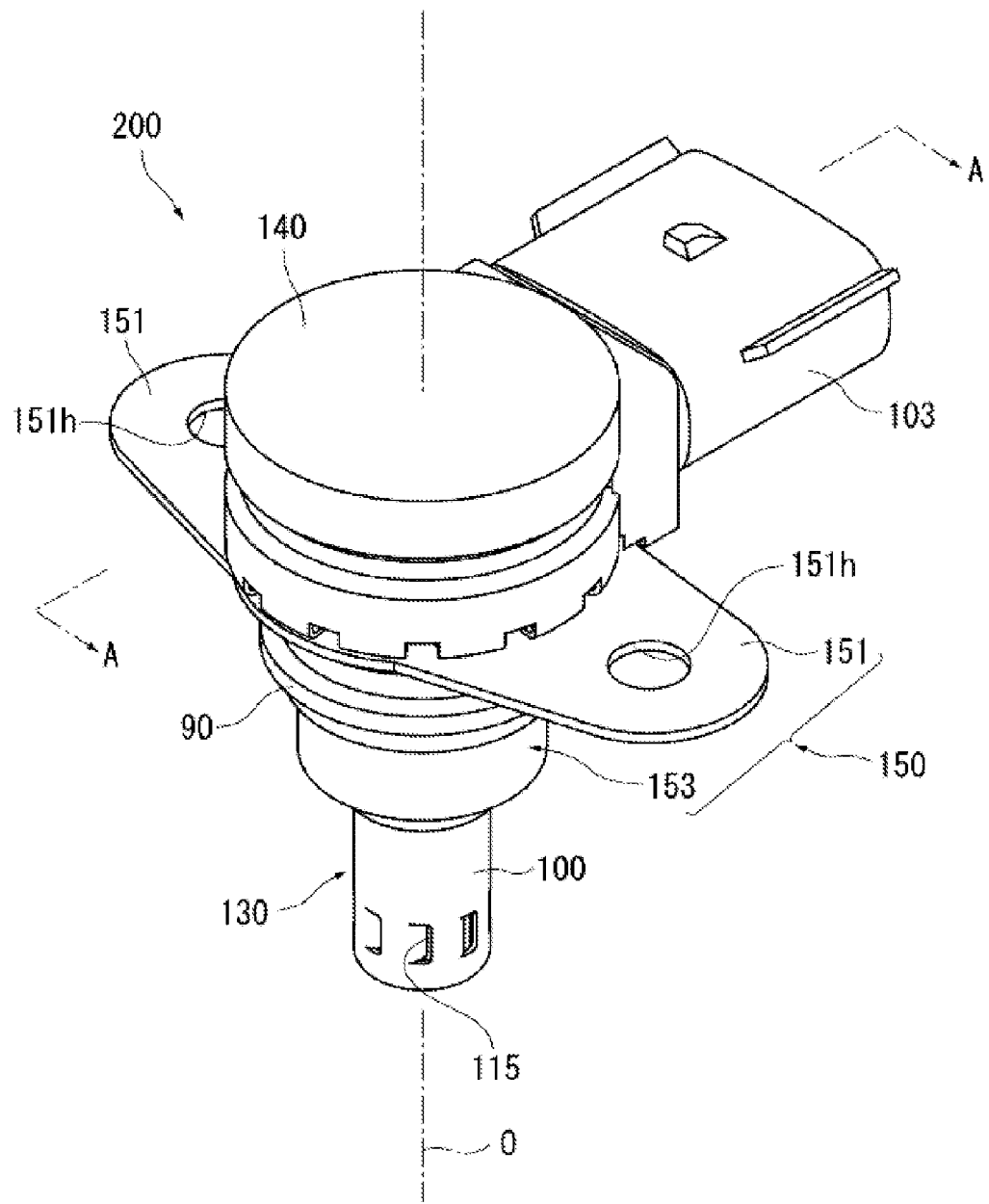
FIG. 1 is a perspective view showing a gas sensor according to a first embodiment of the invention.

Reference numerals used to identify various structural features in the drawings including the following.
200-900: gas sensor
10: gas sensor element
11: detection portion
12: rear end portion of gas sensor element
12a: electrode pad
30-930: connection terminal
31a-961a: elastic portion
31-931: first connection portion
40: separator
42: insertion hole of separator
42a, 42b: surface of separator
50: metallic shell
60-960: connector terminal
61-961: second connection portion
101: body portion
103: connector portion
105, 107, 307, 807: trunk member
107a, 807a: inner surface of trunk member
O: direction of axis

DETAILED DESCRIPTION OF THE PREFERRED EMBODIMENTS

The invention will next be described in greater detail with reference to the drawings. However, the present invention should not be construed as being limited thereto.

Figure 2:
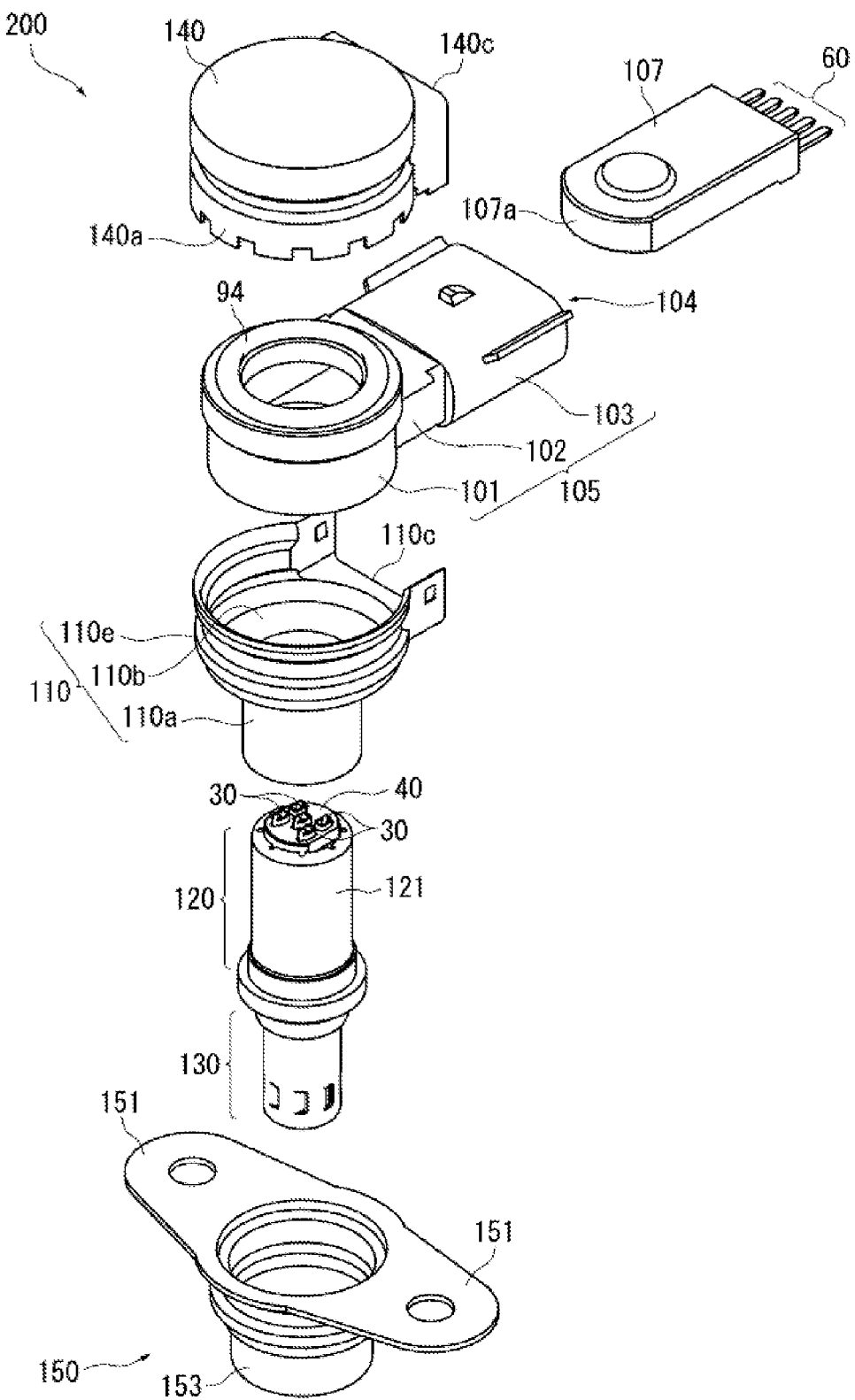
FIG. 2 is an exploded perspective view of the gas sensor.
Figure 3:
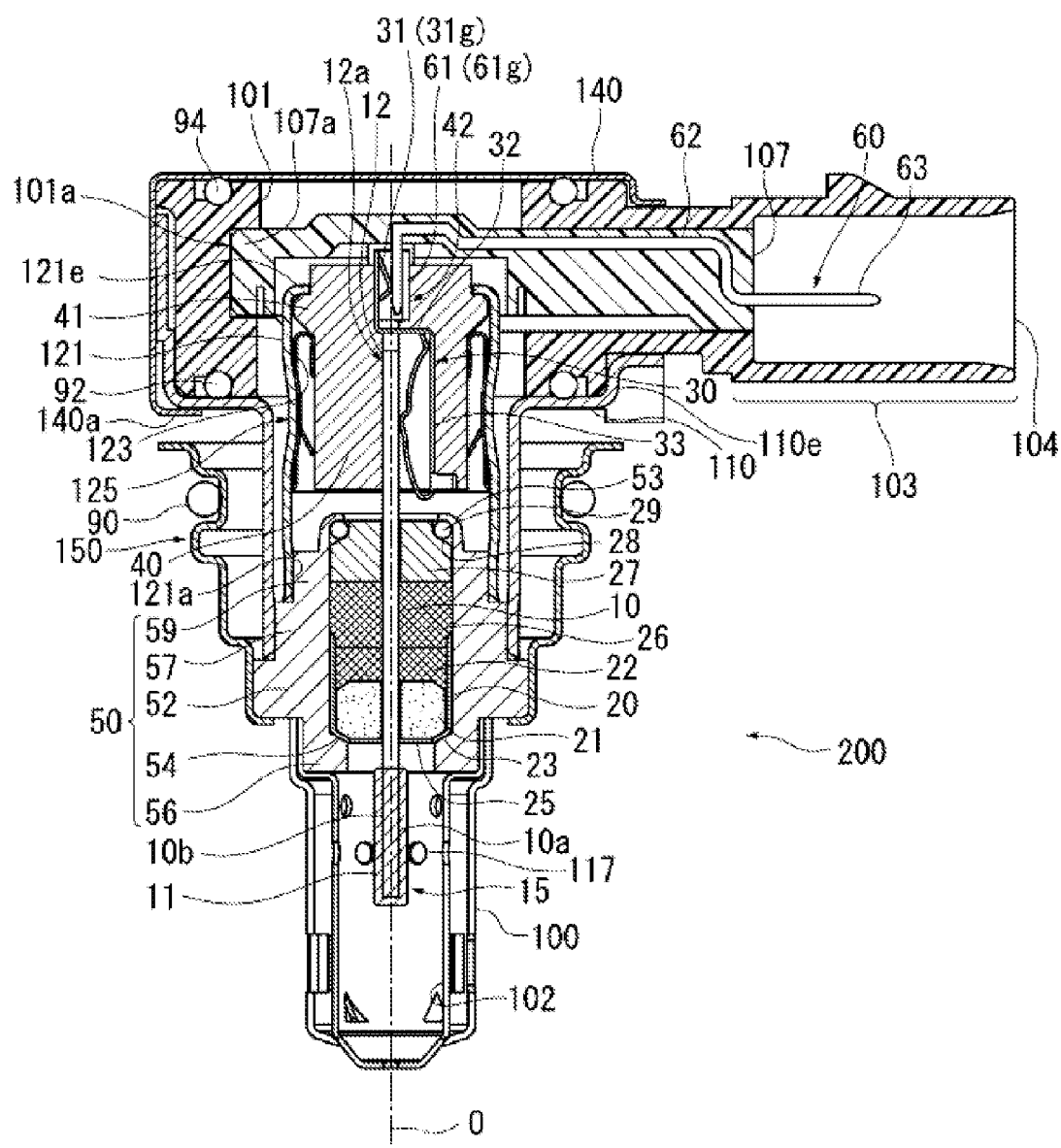
FIG. 3 is a sectional view taken along line A-A of FIG. 1.
Figure 4:
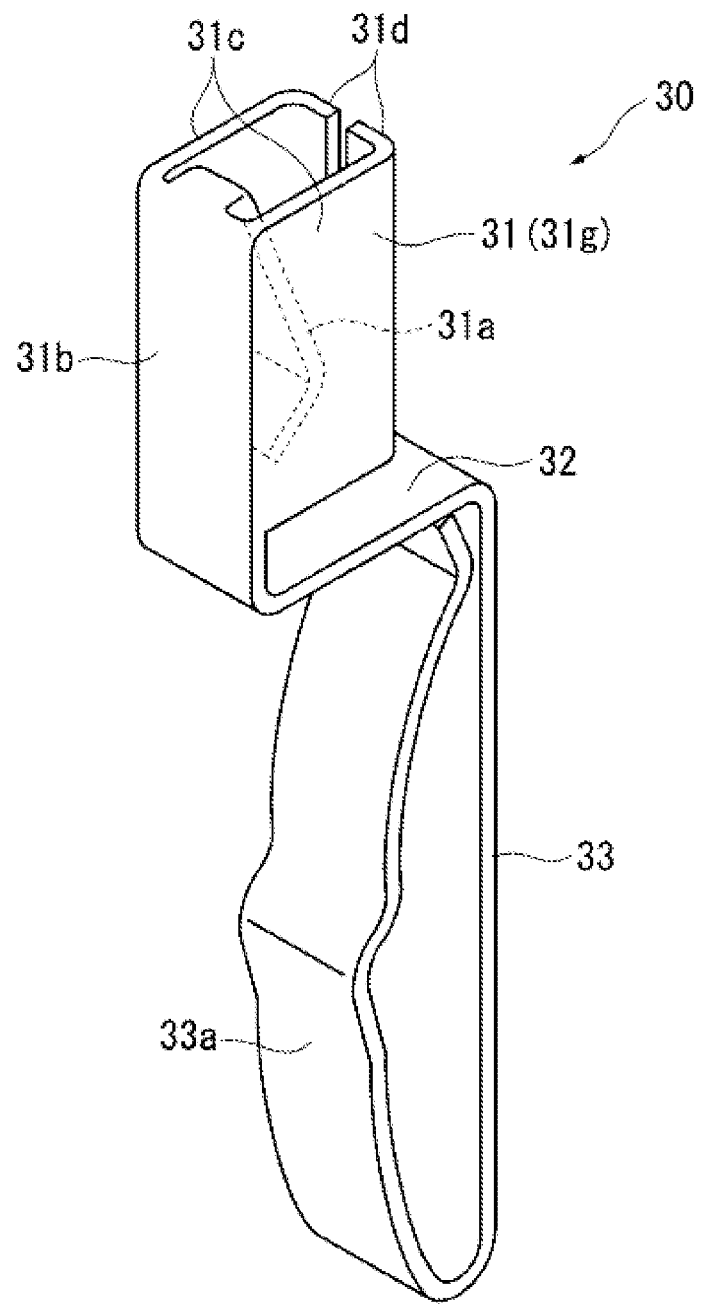
FIG. 4 is an enlarged perspective view of a connection terminal.
Figure 5:
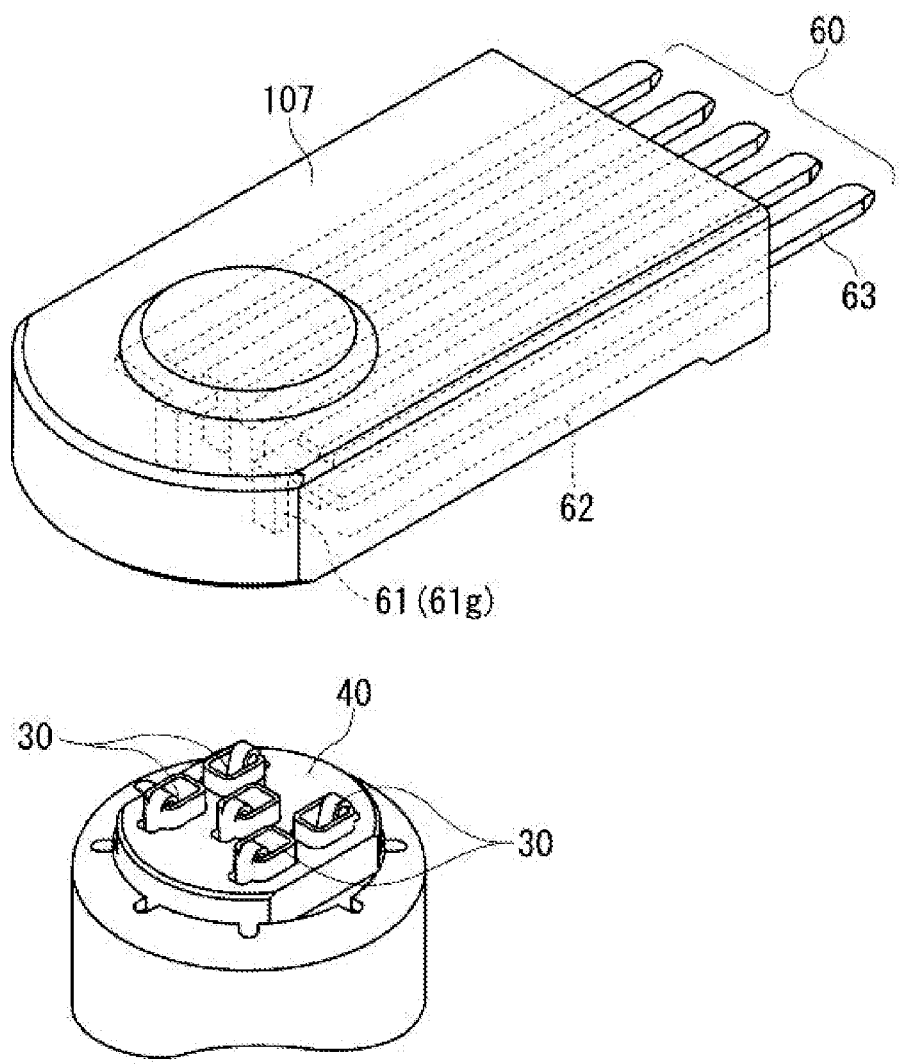
FIG. 5 is an enlarged perspective view of a connector terminal and an insulator.

FIG. 1 is a perspective view of a gas sensor 200 according to a first embodiment of the present invention; FIG. 2 is an exploded perspective view of the gas sensor 200; FIG. 3 is a sectional view taken along line A-A of FIG. 1; FIG. 4 is an enlarged perspective view of a connection terminal 30; and FIG. 5 is an enlarged perspective view of a connector terminal 60 and an insulator 107.

In the drawings, the direction of an axis O (represented by the dash-dot line) of a gas sensor element 10 coincides with the vertical direction. In the following description, a side toward a rear end portion 12 of the gas sensor element 10 is referred to as the rear side of the gas sensor element 10 (and of the gas sensor), and an opposite side toward a detection portion 11 (see FIG. 3) of the gas sensor element 10 is referred to as the forward side of the gas sensor element 10 (and of the gas sensor). A direction perpendicular to the direction of the axis O is referred to as a "radial direction" as appropriate.

Figure 8:
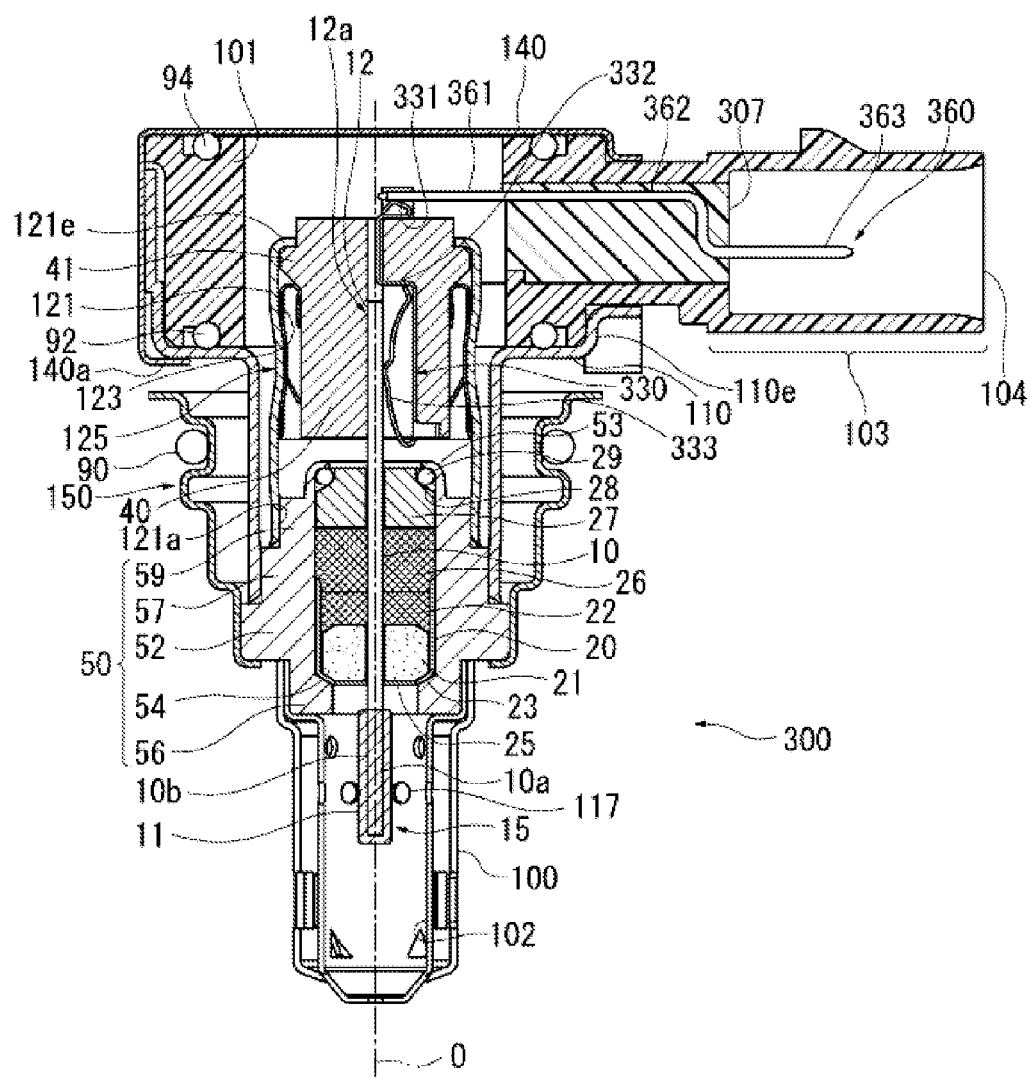
FIG. 8 is a sectional view showing the configuration of a gas sensor according to a second embodiment of the invention.

In FIG. 3 and FIG. 8 and subsequent drawings which correspond thereto, for simplicity, only one connection terminal and only one connecter terminal are shown. However, in actuality, as shown in FIG. 2, FIG. 5, etc., a plurality of connection terminals and a plurality of connecter terminals are provided (in the present embodiment, five connection terminals and five connecter terminals are provided).

As shown in FIGS. 1 and 2, the gas sensor 200 has an element assembly 130 (see FIG. 6(a)) encompassing the gas sensor element 10 and a metallic shell 50; a separator assembly 120 (see FIG. 6(*a*)) fixed to a rear end portion of the element assembly 130; a tubular casing 110 made of metal and surrounding the separator assembly 120; a trunk member 105 having a body portion 101 accommodated in the tubular casing 110, and a connector portion 103 extending from the body portion 101 in a radial direction; an insulator 107 accommodated in the body portion 101 and in the connector portion 103; a metal cover 140 covering the body portion 101; and a flanged casing 150 made of metal and covering a portion of the tubular casing 110.

The flanged casing 150 has a tubular body 153 and a pair of semicircular flange portions 151 extending radially outward from the tubular body 153. Each of the flange portions 151 has a single flange hole 151*h* formed therein. Screws (not shown) are inserted through the respective flange holes 151*h* and are screwed into respective threaded holes provided in an object body (e.g., an intake system of an internal combustion engine) to which the gas sensor 200 is to be mounted, whereby the gas sensor 200 can be mounted to the object body. The tubular body 153 has a recess 153*b* (see FIG. 7(*g*)) formed along the circumferential direction, and a seal member (O-ring) 90 is externally fitted to the recess. Therefore, when the gas sensor 200 is inserted, from its forward end, into an opening of an object body to which the gas sensor is to be mounted, and is then mounted to the object body, the seal member 90 is compressed against a wall surface of the object body, thereby providing a seal between the object body and the flanged casing 150 (tubular body 153).

The trunk member 105 has the body portion 101, a neck portion 102, and the connector portion 103. The body portion 101, the neck portion 102, and the connector portion 103 are integrally formed from an electrically insulating high polymer material (resin) having good formability; for example, NYLON (registered trademark). The trunk member 105 may be formed of another electrically insulating material (e.g., ceramic). Also, in a state in which the insulator 107 is accommodated in the body portion 101 and in the connector portion 103, the insulator 107 is encompassed by the "trunk member 105."

The body portion 101 is formed into a substantially tubular shape so as to laterally surround the separator assembly 120. The substantially rectangularly tubular connector portion 103 extends radially outward from the body portion 101 via the substantially rectangularly tubular neck portion 102. The connector portion 103 is a male connector having an opening 104 which opens radially outward, and allows a mating connector (in this example, a female connector) of an external device to be radially inserted thereinto and removed therefrom through the opening 104.

The insulator 107 is accommodated in the interiors of the body portion 101 and the connector portion 103. In assembling, when the insulator 107 is radially inserted through the opening 104 into the connector portion 103 and into the body portion 101, an end 107*a*, on a side toward the separator 40, of the insulator 107 abuts against an inner surface 101*a* (see FIG. 3) of the body portion 101, whereby the insulator 107 is positioned. The insulator 107 holds a plurality of (in this example, five pieces) the connector terminals 60. The connector terminals 60 extend on the inside and outside of the connector portion 103 in a direction (a radial direction) intersecting with the direction of the axis O. The connector terminals 60 will be described below.

The tubular casing 110 has a front tube 110*a* slightly larger in diameter than the separator assembly 120, and a rear tube 110*e* which is provided at the rear end of the front tube 110*a* and is greater in diameter than the front tube 110*a*. Furthermore, a stepped portion extends radially in such a manner as to connect the front tube 110*a* and the rear tube 110*e*, and serves as a receiving portion 110*b* on which the body portion 101 is placed. A forward portion of the separator assembly 120 is accommodated in the front tube 110*a*, and a rear end portion of the separator assembly 120 protrudes rearward from the front tube 110*a* and is accommodated in the rear tube 110*e* (see FIG. 6(*d*)). Furthermore, the tubular body portion 101 is fitted into an annular space between the rear tube 110*e* and a rear end portion of the separator assembly 120 in such a manner as to be placed on the receiving portion 110*b*, and the body portion 101 thereby surrounds the rear end portion of the separator assembly 120 (and, in turn, a rear end portion of the gas sensor element 10) (see FIG. 7(*e*)).

A rear end portion of the separator 40 is exposed from the rear end of the separator assembly 120, and the connection terminals (in this example, five pieces) 30 protrude rearward from the separator 40 (to be described in detail below).

An extension portion 110*c* having a section resembling a sideways squarish letter U extends radially outward from the rear tube 110*e*. Peripheral edges of the extension portion 110*c* are free ends, and the rear end of the extension portion 110*c* is open. Therefore, when the trunk member 105 is accommodated in the rear tube 110*e*, the body portion 101 is accommodated in the rear tube 110*e*; the neck portion 102 is accommodated in the extension portion 110*c*; and the connector portion 103 protrudes radially outward from the extension portion 110*c*. Also, a rear end portion of the body portion 101 protrudes rearward from the rear tube 110*e*.

A forward end portion of the front tube 110*a* is externally fitted, crimped, and then welded to a diameter-expanded portion 57 of the metallic shell 50 (see FIG. 3), whereby the tubular casing 110 is fixed to the metallic shell 50 (to be described in detail later).

Meanwhile, a closed-bottomed cylindrical metal cover 140 having a closed rear end covers a rear end portion of the body portion 101 radially from the outside. The metal cover 140 is slightly larger in diameter than the rear tube 110*e*. A forward end portion 140*a* of the metal cover 140 extends forward of the receiving portion 110*b* and is, in assembling, bent radially inward and crimped in such a manner as to surround and abut the receiving portion 110*b*. In this manner, the metal cover 140 is fixed to the tubular casing 110 and covers the rear tube 110*e* and the body portion 101. As shown in FIG. 2, the forward end portion 140*a* prior to bending assumes a form consisting of forward protruding ridges and rearward sinking troughs which are alternately formed, and the ridges are bent radially inward (see FIG. 3).

The metal cover 140 covers the outside of the body portion 101 and is connected to the tubular casing 110 connected to the metallic shell 50. Thus, heat from the metallic shell 50 is conducted to the metal cover 140 via the tubular casing 110 and is then radiated outward. Therefore, heat conducted to the body portion 101 residing in the metal cover 140 is reduced, whereby heat deterioration of the body portion 101 (and, in turn, the trunk member 105) can be restrained.

Furthermore, since the body portion 101 is held between the metal cover 140 and the tubular casing 110 (the receiving portion 110*b* of the tubular casing 110), the body portion 101 made of resin is held in the gas sensor 200 without being in direct contact with the metallic shell 50; i.e., in isolation from the metallic shell 50, whereby heat deterioration of the body portion 101 (and, in turn, the trunk member 105 including the connector portion 103) can be further restrained.

The metal cover 140 has an extension portion 140*c* extending radially outward and having a section resembling a sideways squarish letter U. Peripheral edges of the extension portion 140*c* are free ends, and the distal end of the extension portion 140c is open. Also, the extension portion 140c is larger than the extension portion 110c. Therefore, when, with the extension portion 140c oriented in the same direction as that of the extension portion 110c, the metal cover 140 is put on the extension portion 110c from the rear side, the extension portion 140c covers the extension portion 110c, and the connector portion 103 protrudes radially outward from the extension portion 140c.

A seal member (O-ring) 94 is disposed in an annular groove formed on the rear end surface of the body portion 101, thereby providing a gastight seal between the rearward-oriented surface of the body portion 101 and the forward-oriented surface of the metal cover 140. Similarly, a seal member (O-ring) 92 is disposed in an annular groove formed on the forward end surface of the body portion 101 (see FIG. 3), thereby providing a gastight seal between the forward-oriented surface of the body portion 101 and the rearward-oriented surface of the receiving portion 110b. The seal members 92 and 94 have a function of stably holding the body portion 101 between the tubular casing 110 and the metal cover 140 with elastic force.

Next, with reference to FIG. 3, the element assembly 130 and the separator assembly 120 will be described. The element assembly 130 has the gas sensor element 10 and the metallic shell 50.

The gas sensor element 10 is a publicly known substantially rectangular columnar laminate which extends in the direction of the axis O and in which a detection element for detecting an oxygen concentration and a heater for promptly activating the detection element by applying heat are bonded together. The detection element is configured such that a solid electrolyte member which contains zirconia as a main component, and a pair of electrodes which contain platinum as a main component, are laminated together via an insulation layer having a hollow measuring chamber formed therein. More specifically, the detection element has an oxygen pump cell and an oxygen-concentration-measuring cell. The oxygen pump cell is configured as follows: one of a pair of electrodes formed on the respective opposite sides of a solid electrolyte member is exposed outward, whereas the other electrode is exposed to the measuring chamber. The oxygen-concentration-measuring cell is configured as follows: one of a pair of electrodes formed on the respective opposite sides of a solid electrolyte member is exposed to the measuring chamber, whereas the other electrode is exposed to a reference gas chamber. Current to be applied between the paired electrodes of the oxygen pump cell is controlled in such a manner that an output voltage of the oxygen-concentration-measuring cell assumes a predetermined value, thereby pumping oxygen out from the measuring chamber or pumping oxygen into the measuring chamber from outside.

In the oxygen pump cell, the pair of electrodes and a portion of the solid electrolyte member sandwiched between the electrodes collectively serve as the detection portion 11 in which current flows according to the concentration of oxygen. The rear end portion 12 of the gas sensor element 10 has five electrode pads 12a (FIG. 3 shows two of them formed on a second surface 10b of the gas sensor element 10, and the remaining three are formed on a first surface 10a) formed thereon for leading out outputs from the detection element and for supplying power to the heater.

A closed-bottomed tubular metal cup 20 is disposed slightly forward of the axial center of the gas sensor element 10 in such a manner that the gas sensor element 10 is inserted through the interior of the metal cup 20 with the detection portion 11 projecting from an opening 25 formed in the bottom of the metal cup 20. The metal cup 20 is a member for holding the gas sensor element 10 in the metallic shell 50. A forward-end peripheral portion 23 located at a peripheral portion of the bottom of the metal cup 20 is tapered toward a tubular wall portion of the metal cup 20. The metal cup 20 contains a ceramic ring 21 made of alumina and a talc ring 22 formed by compacting a talc powder, in such a manner that the gas sensor element 10 is inserted through the ceramic ring 21 and through the talc ring 22. The talc ring 22 is compressed within the metal cup 20 so as to tightly fill an associated space, thereby holding the gas sensor element 10 in position in the metal cup 20.

An assembly of the metal cup 20 and the gas sensor element 10 is radially surrounded and held by the tubular metallic shell 50. The metallic shell 50 is formed of stainless steel such as SUS430. Specifically, the metallic shell 50 has a stepped portion 54 formed on the inner circumference thereof, and the forward-end peripheral portion 23 of the metal cup 20 which holds the gas sensor element 10 is seated on the stepped portion 54. Furthermore, a talc ring 26 is placed into the metallic shell 50 along the inner circumference of the metallic shell 50 toward the rear end of the metal cup 20 in such a state that the gas sensor element 10 is inserted through the talc ring 26. A tubular sleeve 27 is fitted into the metallic shell 50 so as to press the talc ring 26 from the rear end of the talc ring 26. The sleeve 27 has a step-like shoulder portion 28 formed on the outer circumferential surface of a rear end portion of the sleeve 27. An annular crimp packing 29 is disposed on the shoulder portion 28.

Meanwhile, the metallic shell 50 has a diameter-reduced rear end portion 59 formed at a rear end portion of the outer circumference thereof and has the diameter-expanded portion 57 formed on the forward side of the rear end portion 59 and expanded in diameter stepwise radially outward from the rear end portion 59. Furthermore, the metallic shell 50 has a large-diameter portion 52 and a forward-end engagement portion 56 formed on the forward side of the diameter-expanded portion 57, and an outer protector 100 and an inner protector 102, described below, engage the forward-end engagement portion 56. The metallic shell 50 further has a crimped portion 53 formed on the rear side of the rear end portion 59 for holding the gas sensor element 10 in the metallic shell 50 through crimping.

The crimped portion 53 of the metallic shell 50 is crimped so as to press the shoulder portion 28 of the sleeve 27 forward via the crimp packing 29. By forming the crimped portion 53, the talc ring 26 pressed through the sleeve 27 is compressed within the metallic shell 50, to thereby tightly fill an associated space. By means of the talc ring 26 and the talc ring 22, which is previously placed in the metal cup 20, the metal cup 20 and the gas sensor element 10 are held in position in the metallic shell 50 in a gastight manner.

Meanwhile, the detection portion 11 of the gas sensor element 10 is coated with a porous protection layer 15 so as to protect externally exposed electrodes of the detection portion 11 from becoming poisoned and from water adhesion caused by intake gas or the like. The outer protector 100 and the inner protector 102 are fitted to and fixedly laser-welded to the forward-end engagement portion 56 of the metallic shell so as to protect the detection portion 11 accommodated therein. The outer protector 100 has gas introduction holes 115 formed therein (see FIG. 1), and the inner protector 102 has gas introduction holes 117 formed therein. Thus, adhesion of water and oil contained in gas can be restrained, to thereby restrain generation of a crack or breakage in the gas sensor element 10. Also, adhesion of soot contained in gas to the gas sensor element 10 can be restrained, to thereby restrain deterioration in gas detection accuracy of the gas sensor 200.

Next, the separator assembly 120 will be described. The separator assembly 120 includes the separator 40, a metal inner tube 121, a holding member 123, and the connection terminals 30, and is disposed on the rear side of the metallic shell 50. The separator assembly 120 has a crimped portion 125 which is located in a substantially central region with respect to the direction of the axis O and unitarily fixes the metal inner tube 121 and the holding member 123 by radially inward crimping from a radially outside direction.

The separator 40 is formed into a substantially cylindrical shape from an electrically insulating ceramic or resin. The separator 40 has a collar portion 41 protruding radially outward and an insertion hole 42 extending therethrough in the direction of the axis O. The connection terminals 30 are inserted into the insertion hole 42 at respectively predetermined positions and are accommodated in the separator 40 while being isolated from one another so as to avoid mutual contact. The rear end portion 12 of the gas sensor element 10 is inserted into the insertion hole 42, and elastic portions 33a (see FIG. 4) of forward portions 33 of the connection terminals 30 are electrically connected to the electrode pads 12a, respectively, of the gas sensor element 10.

A rear end portion of the separator 40 is exposed from the rear end of the separator assembly 120, and first connection portions 31 (in this example, five pieces) of the connection terminals 30 protrude rearward from the rearward-oriented surface of the separator 40.

A forward end portion 121a of the metal inner tube 121 is crimped and fixedly welded to the rear end portion 59 of the metallic shell 50 while covering the rear end portion 59. Meanwhile, a rear end portion 121e of the metal inner tube 121 is bent radially inward and thereby engaged with the collar portion 41. Also, the separator 40 and the holding member 123 are disposed inside the metal inner tube 121, and the rearward-oriented surface of the holding member 123 abuts against the collar portion 41. The holding member 123 is a tubular member made of metal and urges the separator 40 radially inward and the collar portion 41 rearward with the elastic force of a bent rear end portion thereof. Also, the holding member 123, together with the metal inner tube 121, is crimped radially inward from outside the metal inner tube 121, thereby forming the crimped portion 125 and being fixed to the metal inner tube 121.

The separator 40 is not fixed directly to the metallic shell 50 and to the metal inner tube 121, but is fixedly held within the metal inner tube 121 by means of the metal inner tube 121 and the holding member 123. By employing such a configuration, poor contact between the connection terminals 30 and the connector terminals 60 is restrained which could otherwise result from vibration or positional shift of the separator 40 induced by vibration or impact imposed on the gas sensor 200.

Next, with reference to FIGS. 4 and 5, the connection terminals 30 and the connector terminals 60, which are characteristic features of the first embodiment, will be described. The connection terminal 30 of FIG. 4 is the center-disposed connection terminal 30 of the five connection terminals 30 shown in FIGS. 2 and 5.

As shown in FIG. 4, the connection terminal 30 has a first connection portion 31 extending in the direction of the axis O, a plate-like intermediate portion 32 radially extending on the forward side of the first connection portion 31, and a forward portion 33 extending in the direction of the axis O on the forward side of the intermediate portion 32. The connection terminal 30 is formed into a shape resembling a crank as viewed laterally. The first connection portion 31 has a main portion 31b bent from the intermediate portion 32 in a shape of letter L and standing upright in the direction of the axis O; side portions 31c bent from widthwise opposite ends of the main portion 31b in a shape of letter L and extending radially; and opposed portions 31d bent from the side portions 31c along the main body 31b in a shape of letter L and approaching each other. The first connection portion 31 is a boxlike female portion 31g having a substantially rectangular section. Furthermore, the first connection portion 31 has an elastic portion 31a bent forward from the rear end of the main portion 31b. The elastic portion 31a is located within the boxlike first connection portion 31 and elastically bends toward the main portion 31b. The elastic portion 31a is a spring portion whose forward end is a free end. By assuming the form of the spring portion, the elastic portion 31a increases in elastic force, so that the first connection portion 31 and a second connection portion 61 are reliably connected. As described below, the direction in which the elastic portion 31a elastically bends intersects with a direction of juxtaposition of the first connection portion 31 and the second connection portion 61 (in the first embodiment, the direction of the axis O). The forward portion 33 has an elastic portion 33a bent rearward from the forward end of the forward portion 33. The elastic portion 33a is pressed against the corresponding electrode pad 12a of the gas sensor element 10, to thereby establish an electrical connection.

The connection terminal 30 of FIG. 4 has the intermediate portion 32; however, of the five connection terminals 30 shown in FIGS. 2 and 5, the four connection terminals 30 other than the center one do not have the intermediate portion 32. Whether or not the intermediate portion 32 is provided may be determined as appropriate according to the relative position between the first connection portion 31 and the forward portion 33.

In the connection terminal 30, a rear end portion of the first connection portion 31 protrudes rearward from the rearward-oriented surface of the separator 40, and the remaining portion is held within the insertion hole 42 of the separator 40.

Meanwhile, as shown in FIG. 5, the connector terminals (in this example, five pieces) 60 are held in the insulator 107 while being separated from one another. Each of the connector terminals 60 has a plate-like intermediate portion 62 extending radially and embedded in the insulator 107; the second connection portion 61, which is an end portion extending from the intermediate portion 62 toward the separator 40, having an insertion piece 61g bent from the intermediate portion 62 in a shape of letter L and extending in the direction of the axis O; and a male portion 63 protruding radially outward from the insulator 107. A male connector is formed by male portions 63 protruding from the insulator 107. Although unillustrated in FIG. 5, as shown in FIG. 3, the intermediate portion 62 is bent in a shape resembling a crank and connected to the male portion 63, and the male portion 63 extends in parallel with the intermediate portion 62 and is located forward of the intermediate portion 62 (i.e., at substantially the center of the connector portion 103 with respect to the direction of the axis O).

As will be described in detail with reference to FIG. 6, in the first embodiment, the trunk member 105 (the body portion 101 thereof) is fitted, from the rear side, into the rear tube 110e to which the separator assembly 120 is assembled (see FIG. 6(d)). At this time, the insertion pieces 61g reside around the axis of the body portion 101 and are disposed at positions which face the connection terminals 30 protruding rearward from the separator 40.

Thus, when the trunk member 105 is fitted into the rear tube 110e, the second connection portions 61 are inserted (fitted) into the corresponding first connection portions 31 (the insertion pieces 61g are fitted into the corresponding female portions 31g) from the direction of the axis O and press the corresponding elastic portions 31a, so that the elastic portions 31a elastically bend in a radial direction. As a result, the first connection portions 31 and the second connection portions 61 are elastically connected, respectively. Thus, detection outputs from the gas sensor element 10 can be led out to the connector terminals 60 via the connection terminals 30. Therefore, in the lateral-lead-out-type gas sensor, the connection terminals 30 and the connector terminals 60 can be electrically connected without welding, and productivity can thereby be improved. Also, a lead frame for welding the connection terminals 30 and the connector terminals 60 becomes unnecessary, and the number of components is thereby reduced.

In the first embodiment, the second connection portions 61 are bent and extend in the direction of the axis O in such a manner as to be juxtaposed with the first connection portions 31, whereby the first connection portions 31 and the corresponding second connection portions 61 can be connected.

As shown in the first embodiment, each of the second connection portions 61 has the insertion piece 61g, and each of the first connection portions 31 has the female portion 31b. That is, the first connection portion 31 having the female portion 31g is fixed to the separator 40, and the second connection portion 61 is fitted into the first connection portion 31, thereby connecting the first connection portion 31 and the second connection portion 61. Thus, by virtue of the second connection portion 61 assuming the form of the insertion piece 61g, the second connection portion 61 does not come into contact with the separator 40, whereby chipping of the separator 40 can be prevented.

Also, each of the second connection portions 61 has the insertion piece 61g which extends in the direction of the axis O through bending, and the female portion 31g of each of the first connection portions 31 resides within the insertion hole 42. Thus, since the female portion 31g of the first connection portion 31 is fixed in the insertion hole 42 extending in the direction of the axis O, and the second connection portion 61 is inserted into the female portion 31g, insertion (fitting) is facilitated and ensured.

Since the gas sensor element 10 assumes a high temperature as a result of heating by its own heater and exposure to, for example, exhaust gas, in the first embodiment, the connection terminals 30 connected to the gas sensor element 10 are formed of a material having a heat resistance higher than that of a material used to form the connector terminals 60. In this case, since the connection terminals 30 and the connector terminals 60 differ in material, some difficulty is encountered in welding them together. However, in the present invention, there is no need to weld the connection terminals 30 and the connector terminals 60. Therefore, even though different materials are used to form the connection terminals 30 and the connector terminals 60, electrical connection can be easily established therebetween.

The connection terminals 30 can be formed of stainless steel or an Ni-based alloy (e.g., SUS631 or INCONEL (registered trademark)), which is a heat resisting metal. The connector terminals 60 can be formed of a copper-based material, such as brass.

Next, with reference to FIGS. 6 and 7, an example method of manufacturing the gas sensor 200 according to the first embodiment of the present invention will be described.

First, the element assembly 130 is fabricated by a publicly known method. Also, as mentioned above, the connection terminals 30 are inserted into and held in the insertion hole 42 of the separator 40. The thus-prepared separator 40 and the holding member 123 are accommodated in the metal inner tube 121. Then, crimping is performed from radially outside on the metal inner tube 121 at a substantially central portion with respect to the direction of the axis O so as to fix the holding member 123 within the metal inner tube 121 and to hold the separator 40, thereby yielding the separator assembly 120.

Next, as shown in FIG. 6(a), the separator assembly 120 is fitted, from its forward end, to the rear end of the element assembly 130, and the rear end portion 12 of the gas sensor element 10 is thereby inserted into the insertion hole 42 of the separator 40. By this procedure, forward portions (not shown) of the connection terminals 30 are electrically connected to the corresponding electrode pads 12a of the gas sensor element 10. Also, the forward end portion 121a of the metal inner tube 121 is externally fitted to the rear end portion 59 of the metallic shell 50 and abuts against a stepped portion between the rear end portion 59 and the diameter-expanded portion 57, to thereby position the same. In this condition, the forward end portion 121a is crimped from radially outside and welded, whereby the separator assembly 120 is fixed to the metallic shell 50; i.e., to the element assembly 130.

Next, as shown in FIG. 6(b), the tubular casing 110 is inserted, from its forward end, into the separator assembly 120, whereby a forward portion of the separator assembly 120 is accommodated in the front tube 110a, and a forward end portion of the front tube 110a is externally fitted to the diameter-expanded portion 57 of the metallic shell 50 and abuts against a stepped portion between the diameter-expanded portion 57 and the large-diameter portion 52, to thereby position the same. In this condition, the forward end portion of the front tube 110a is crimped from radially outside and welded, whereby the tubular casing 110 is fixed to the metallic shell 50.

Next, as shown in FIG. 6(c), the insulator 107 having the connector terminals 60 held therein is radially inserted into the connector portion 103 from the opening 104, whereby the end 107a of the insulator 107 abuts against the inner surface 101a of the body portion 101, and the insulator 107 is thereby positioned. At this time, the insertion pieces 61g of the second connection portions 61 located toward the end 107a of the insulator 107 are disposed around the axis of the body portion 101.

Then, as shown in FIG. 6(d), the trunk member 105 is inserted, from its forward end, into the tubular casing 110 (the rear tube 110e thereof), whereby the separator 40 is positioned on the axis of the rear tube 110e. Then, the trunk member 105 (the body portion 101 thereof) is placed on the receiving portion 110b via the seal member 92. By this procedure, the second connection portions 61 of the connector terminals 60 are fitted into the corresponding first connection portions 31 of the connection terminals 30 protruding from the separator 40 (the insertion pieces 61g are fitted into the corresponding female portions 31g), whereby the connection terminals 30 and the connector terminals 60 can be electrically connected without welding.

Next, as shown in FIG. 7(e), the metal cover 140 is externally fitted, from its forward opening portion, to the tubular casing 110 (the outer tube 110e thereof) via the seal member 94. Then, as shown in FIG. 7(f), the ridges of the forward end portion 140a of the metal cover 140 are bent and crimped radially inward in such a manner as to surround the receiving portion 110b, whereby the metal cover 140 is fixed to the tubular casing 110, and the body portion 101 is held between the tubular casing 110 (the receiving portion 110b thereof) and the metal cover 140. In this manner, the metal cover 140 covers the rear tube 110e and the body portion 101.

Next, as shown in FIG. 7(g), the flanged casing 150 is externally fitted, from its rear end, to the element assembly 130, whereby a flat portion 153a extending radially inward and provided at the forward end of the tubular body 153 of the flanged casing 150 abuts against a stepped portion of the metallic shell 50 between the large-diameter portion 52 and the forward-end engagement portion 56, to thereby position the same. In this condition, the tubular body 153 is crimped from radially outside and welded at a portion corresponding to the large-diameter portion 52, whereby the flanged casing 150 is fixed to the metallic shell 50; i.e., to the element assembly 130.

Furthermore, as shown in FIG. 7(h), the seal member (O-ring) 90 is externally fitted into the recess 153b, to thereby complete the gas sensor 200.

Examples of an object body to which the gas sensor 200 is to be mounted include various internal combustion engines; particularly, intake systems of internal combustion engines of vehicles, such as automobiles. The intake system is an intake path extending from an intake to an intake port of an internal combustion engine; for example, an intake pipe or an intake manifold, which branches off from the intake pipe and is connected to the intake port of the internal combustion engine. Intake gas encompasses fresh air (fresh air which does not contain exhaust) and a mixed gas of fresh air and exhaust refluxed (recirculated) to the intake system.

The gas sensor element 10 of the present embodiment is a so-called full range air/fuel ratio sensor. However, in addition to the full range air/fuel ratio sensor, the present invention may also be applied, for example, to an oxygen sensor ($\lambda$ sensor) and an NOx sensor.

As compared with control of an internal combustion engine on the basis of the concentration of a particular gas contained in exhaust detected by a gas sensor provided in an exhaust system, control of the internal combustion engine on the basis of the concentration of a particular gas detected by a gas sensor provided in an intake system exhibits higher accuracy of control of the internal combustion engine. This is because control on the basis of the concentration of a particular gas contained in exhaust is a feedback control, whereas control on the basis of the concentration of a particular gas in the intake system is a precombustion control.

Next, with reference to FIGS. 8 and 9, the configuration of a gas sensor 300 according to a second embodiment of the present invention will be described. The gas sensor 300 is similar to the gas sensor of the first embodiment except that the connection terminals 30, the connector terminals 60, and the insulator 107 in the first embodiment are replaced with connection terminals 330, connector terminals 360, and an insulator 307, respectively. Thus, configurational features similar to those of the first embodiment are denoted by like reference numerals, and a detailed description thereof is omitted.

FIG. 8 is a sectional view showing the configuration of the gas sensor 300 and corresponds to FIG. 3 of the first embodiment. In FIG. 8, the connection terminal 330 has a first connection portion 331 extending in the direction of the axis O; a plate-like intermediate portion 332 bent from the forward end of the first connection portion 331 in a shape of letter L and extending radially; and a forward portion 333 extending forward from the intermediate portion 332 in the direction of the axis O. The connection terminal 330 is formed into a shape resembling a crank as viewed laterally, and the forward portion 333 is similar to the forward portion 33 of the first embodiment.

Figure 9:
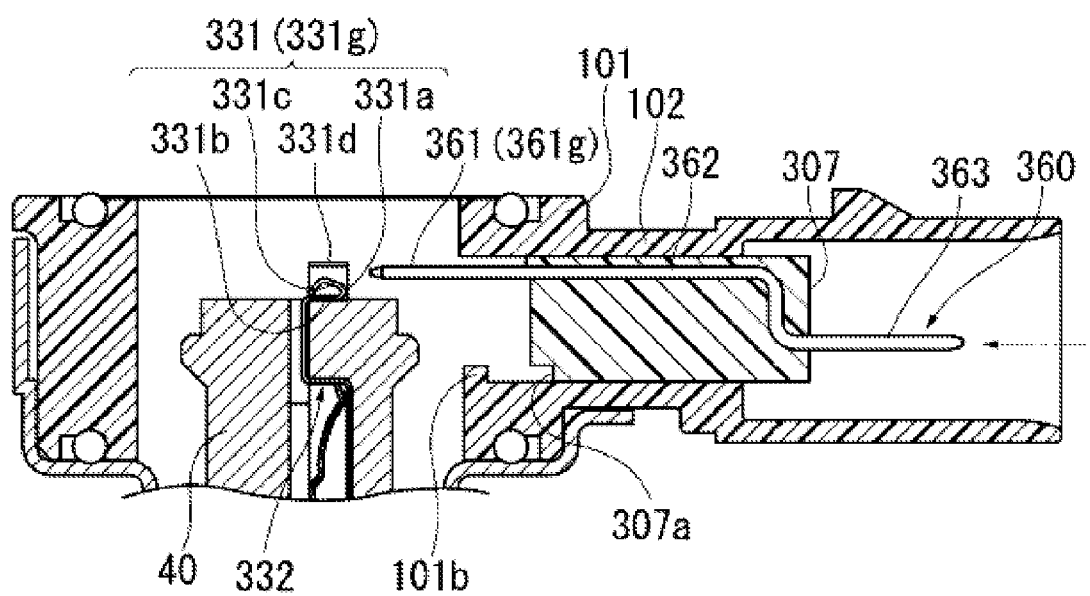
FIG. 9 is a process drawing showing a form of connection between a first connection portion and a second connection portion in the second embodiment.

As shown in FIG. 9, the first connection portion 331 is bent from the intermediate portion 332 in a shape of the letter L and extends in the direction of the axis O, and has, at its rear end portion, a female portion 331g bent in a shape of the letter L and extending radially. The female portion 331g protrudes rearward from the rearward-oriented surface of the separator 40. The female portion 331g has a main portion 331b; a side portion 331c bent from one widthwise (radial) end of the main portion 331b in a shape of the letter L and extending rearward; and a counter portion 331d bent from the side portion 331c in a shape of the letter L along the main portion 331b. Thus, the female portion 331g has a section resembling a sideways squarish letter U. Furthermore, a radially outward end portion of the main portion 331b is bent back in a radially opposite direction so as to form an elastic portion 331a. The elastic portion 331a is located within the first connection portion 331 having a shape resembling a sideways squarish letter U and elastically bends toward the main portion 331b (i.e., forward).

Meanwhile, the connector terminals (in this example, five pieces) 360 are held in the insulator 307 while being separated from one another. Each of the connector terminals 360 has a plate-like intermediate portion 362 extending radially and embedded in the insulator 307; a second connection portion 361, which is an end portion protruding from the intermediate portion 362 toward the separator 40, extending in parallel with the intermediate portion 362; and a male portion 363 connected to the intermediate portion 362 and protruding radially outward from the insulator 307. The male portion 363 and the intermediate portion 362 are similar to those of the first embodiment.

As shown in FIG. 9, the second embodiment differs from the first embodiment in that the direction of insertion (fitting) of the connector terminal 360 (the second connection portion 361 thereof) into the first connection portion 331 is a radial direction.

That is, the first connection portion 331 (the female portion 331g) opens radially and allows the connector terminal 360 (the second connection portion 361 (an insertion piece 361g) thereof) to be radially inserted thereinto. Meanwhile, the insulator 307 has a cut 307a formed on the forward-oriented surface of its end portion on a side toward the separator 40. Also, the body portion 101 has a protrusion 101b corresponding to the cut 307a and formed on its end portion on a side toward the neck portion 102. The manufacturing method slightly differs from that of the first embodiment. After assembling the separator assembly 120, the element assembly 130, and the tubular casing 110, the body portion 101 (the trunk member 105) in a state before attachment of the insulator 307 thereto is fitted into the rear tube 110e. Subsequently, the insulator 307 is radially inserted into the connector portion 103 from the opening 104. By this procedure, the cut 307a abuts against the protrusion 101b, whereby the insulator 307 is positioned; the second connection portion 361 (the insertion piece 361g) is fitted into the first connection portion 331 (the female portion 331g) and presses the elastic portion 331a, and the elastic portion 331a thereby elastically bends in the direction of the axis O. As a result, the first connection portion 331 and the second connection portion 361 are elastically connected. Thus, the connection terminal 330 and the connector terminal 360 can be electrically connected without welding.

In the second embodiment, the direction in which the elastic portion 331a elastically bends intersects with a direction of juxtaposition of the first connection portion 331 and the second connection portion 361 (radial direction) (i.e., the intersecting direction is the direction of the axis O). Also, the first connection portion 331 is bent radially and is thereby juxtaposed with the second connection portion 361, whereby the first and second connection portions 331 and 361 can be connected.

Next, with reference to FIGS. 10 and 11, the configuration of a gas sensor 400 according to a third embodiment of the present invention will be described. The gas sensor 400 is similar to the gas sensor of the first embodiment except that the connection terminals 30 and the connector terminals 60 in the first embodiment are replaced with connection terminals 430 and connector terminals 460, respectively. Thus, configurational features similar to those of the first embodiment are denoted by like reference numerals, and a detailed description thereof is omitted.

Figure 10:
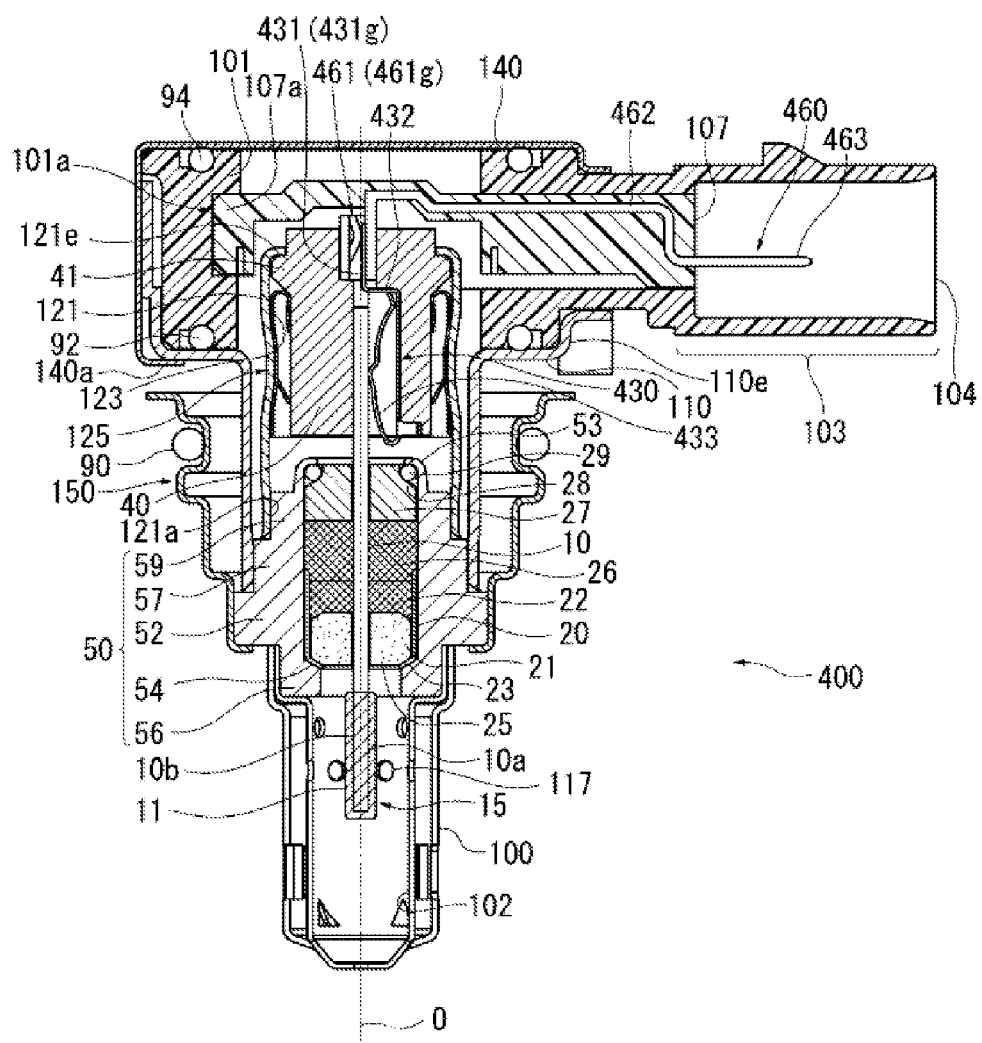
FIG. 10 is a sectional view showing the configuration of a gas sensor according to a third embodiment of the invention.

FIG. 10 is a sectional view showing the configuration of the gas sensor 400 and corresponds to FIG. 3 of the first embodiment. In FIG. 10, the connection terminal 430 has a first connection portion 431 extending in the direction of the axis O; a plate-like intermediate portion 432 bent from the forward end of the first connection portion 431 in a shape of the letter L and extending radially; and a forward portion 433 bent forward from the intermediate portion 432 in a shape of the letter L and extending in the direction of the axis O. The connection terminal 430 is formed into a shape resembling a crank as viewed laterally, and the forward portion 433 is similar to the forward portion 33 of the first embodiment.

In the connection terminal 430, a rear end portion of the first connection portion 431 protrudes rearward from the rearward-oriented surface of the separator 40, and a forward portion of the first connection terminal 431, the intermediate portion 432, and the forward portion 433 are held within the insertion hole 42 of the separator 40. However, the forward portion of the first connection terminal 431 resides within the insertion hole 42 and is separated from the inner surface of the insertion hole 42.

Meanwhile, the connector terminals (in this example, five pieces) 460 are held in the insulator 107 while being separated from one another. Each of the connector terminals 460 has a plate-like intermediate portion 462 extending radially and embedded in the insulator 107; a second connection portion 461, which is an end portion extending toward the separator 40, having a female portion 461g bent from the intermediate portion 462 in a shape of the letter L and extending in the direction of the axis O; and a male portion 463 connected to the intermediate portion 462 and protruding radially outward from the insulator 107. The male portion 463 and the intermediate portion 462 are similar to those of the first embodiment.

Figure 11:
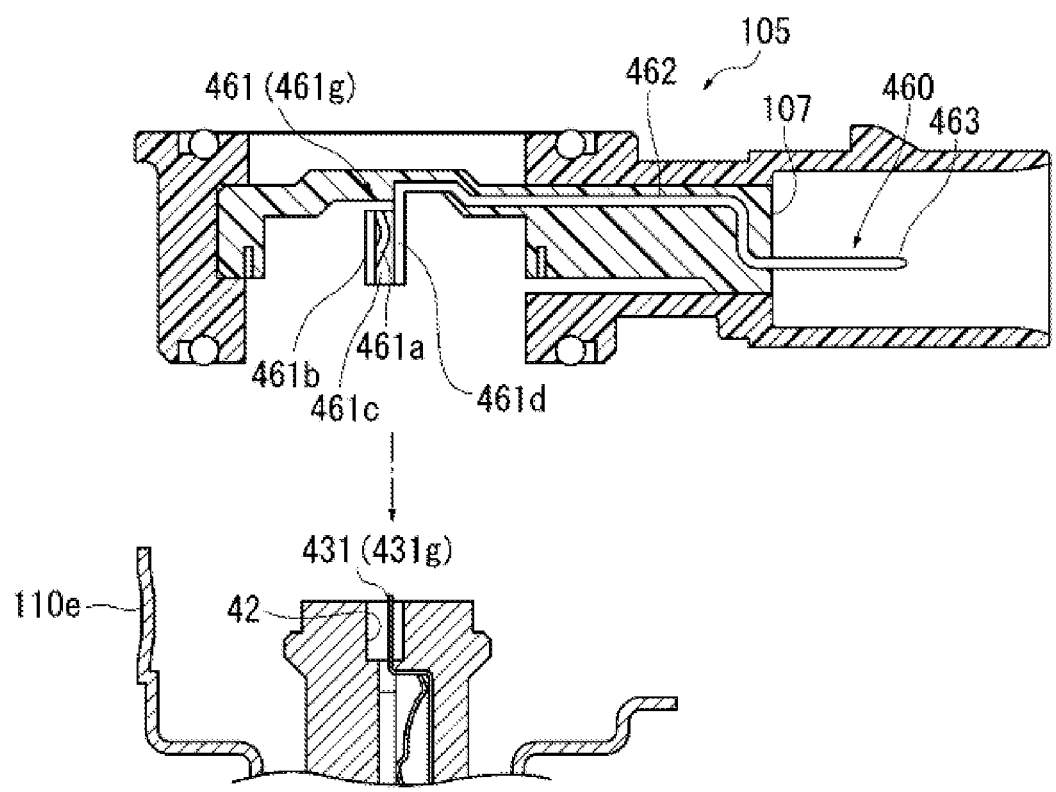
FIG. 11 is a process drawing showing a form of connection between a first connection portion and a second connection portion in the third embodiment.

As shown in FIG. 11, the female portion 461g has a counter portion 461d connected to the intermediate portion 462 and bent in the direction of the axis O in a shape of the letter L; side portions 431c bent from widthwise opposite ends of the counter portion 461d in a shape of the letter L and extending radially; and main portions 461b bent from the side portions 431c along the opposite surface in a shape of the letter L and approaching each other. Furthermore, the female portion 461g has an elastic portion 461a bent rearward from the forward end of the main portion 461b. The elastic portion 461a is located between the main portion 461b and the counter portion 461d and elastically bends toward the main portion 461b (radial direction).

As shown in FIG. 11, the third embodiment differs from the first embodiment in that the first connection portion 431 (insertion piece 431g) is inserted into the connector terminal 460 (the female portion 461g of the second connection portion 461). However, the direction of insertion (fitting) is the same as that of the first embodiment; i.e., the direction of the axis O. That is, the insertion piece 431g can be inserted, in the direction of the axis O, between the main portion 461b and the counter portion 461d of the female portion 461g. Meanwhile, in the third embodiment, the insulator 107 and the body portion 101, to which the insulator 107 is assembled, are similar to those of the first embodiment. Similar to the first embodiment, the trunk member 105 (the body portion 101 thereof) is fitted, from the rear side, into the rear tube 110e to which the separator assembly 120 is assembled (see FIG. 6(d)). At this time, the female portion 461g of the second connection portion 461 is inserted into the insertion hole 42 of the separator 40, and the first connection portion 431 residing in the insertion portion 42 is inserted (fitted) into the second connection portion 461 (the insertion piece 431g is fitted into the female portion 461) in the direction of the axis O and presses the elastic portion 461a. Thus, the elastic portion 461a elastically bends in a radial direction. As a result, the first connection portion 431 and the second connection portion 461 are elastically connected. Further, the connection terminal 430 and the connector terminal 460 can be electrically connected without welding.

Incidentally, the counter portion 461d of the female portion 461g elastically bends in a radial direction. However, when the second connection portion 461 is inserted into the insertion hole 42 of the separator 40, the main portion 461b and the counter portion 461d come into contact with the inner surface of the insertion hole 42. Therefore, the distance between the main portion 461b and the counter portion 461d does not expand, whereby the first connection portion 431 can be reliably held therebetween.

In the third embodiment, the direction in which the elastic portion 461a elastically bends intersects with a direction of juxtaposition of the first connection portion 431 and the second connection portion 461 (the direction of the axis O). Also, the second connection portion 461 is bent in the direction of the axis O and is thereby juxtaposed with the first connection portion 431, whereby the first and second connection portions 431 and 461 can be connected.

Next, with reference to FIGS. 12 and 13, the configuration of a gas sensor 500 according to a fourth embodiment of the present invention will be described. The gas sensor 500 is similar to the gas sensor of the second embodiment except that the connection terminals 330 and the connector terminals 360 in the second embodiment are replaced with connection terminals 530 and connector terminals 560, respectively. Thus, configurational features similar to those of the second embodiment are denoted by like reference numerals, and a detailed description thereof is omitted.

Figure 12:
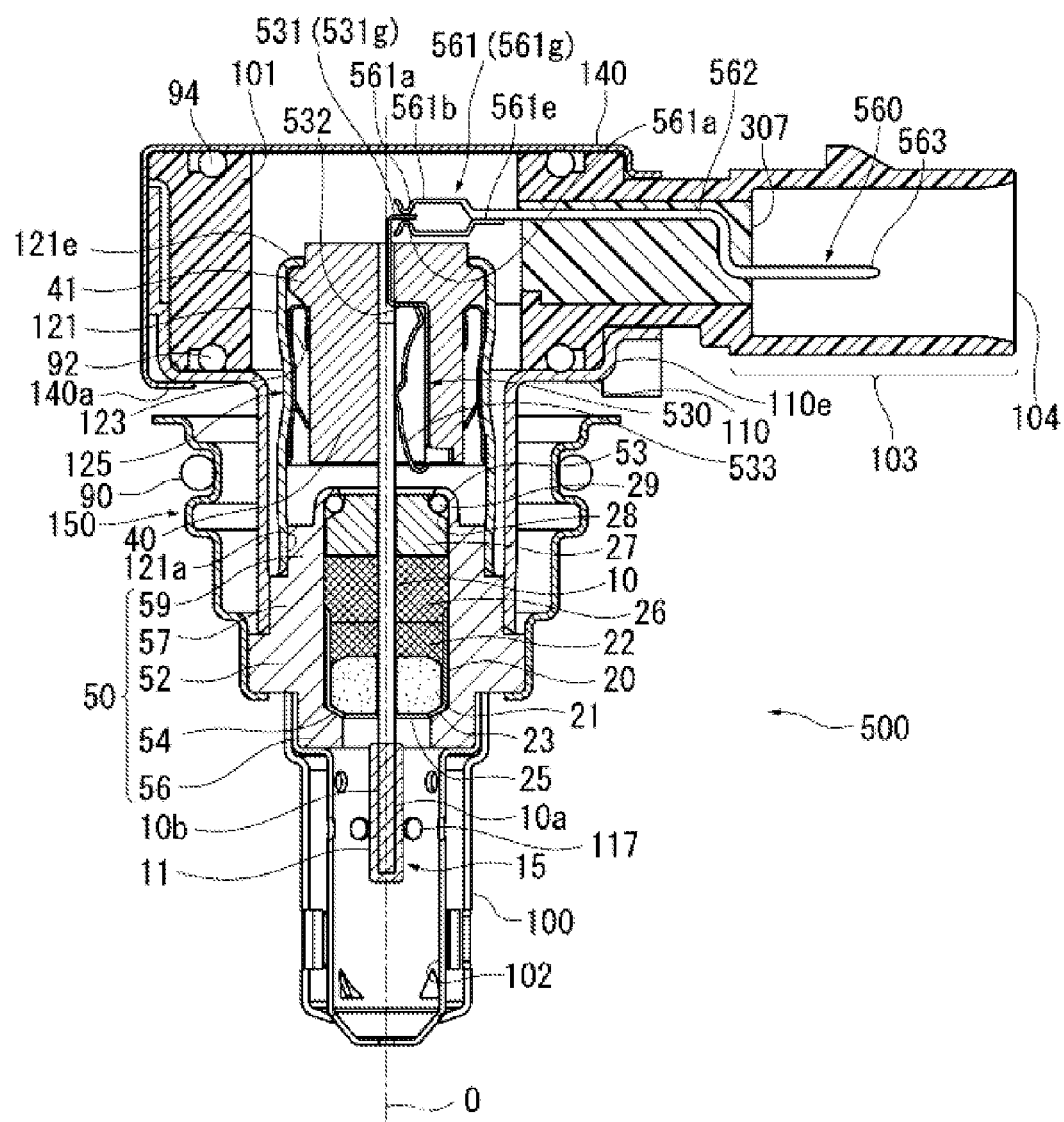
FIG. 12 is a sectional view showing the configuration of a gas sensor according to a fourth embodiment of the invention.

FIG. 12 is a sectional view showing the configuration of the gas sensor 500 and corresponds to FIG. 8 showing that of the second embodiment. In FIG. 12, the connection terminal 530 has a first connection portion 531 extending in the direction of the axis O; a plate-like intermediate portion 532 bent from the first connection portion 531 in a shape of the letter L and extending radially; and a forward portion 533 bent forward from the intermediate portion 532 in a shape of the letter L and extending in the direction of the axis O. The connection terminal 530 is formed into a shape resembling a crank as viewed laterally, and the forward portion 533 is similar to the forward portion 333 of the second embodiment.

As shown in FIG. 12, the first connection portion 531 is bent from the intermediate portion 532 in a shape of the letter L and extends in the direction of the axis O, and has, at its rear end portion, an insertion piece 531g bent in a shape of the letter L and extending radially. The insertion piece 531g protrudes rearward from the rearward-oriented surface of the separator 40.

Meanwhile, the connector terminals (in this example, five pieces) 560 are held in the insulator 307 while being separated from one another. Each of the connector terminals 560 has a plate-like intermediate portion 562 extending radially and embedded in the insulator 307; a second connection portion 561, which is an end portion protruding from the intermediate portion 562 toward the separator 40, extending in parallel with the intermediate portion 562; and a male portion 563 connected to the intermediate portion 562 and protruding radially outward from the insulator 307. The male portion 563 and the intermediate portion 562 are similar to those of the second embodiment. Also, the insulator 307 is similar to that of the second embodiment.

Figure 13:
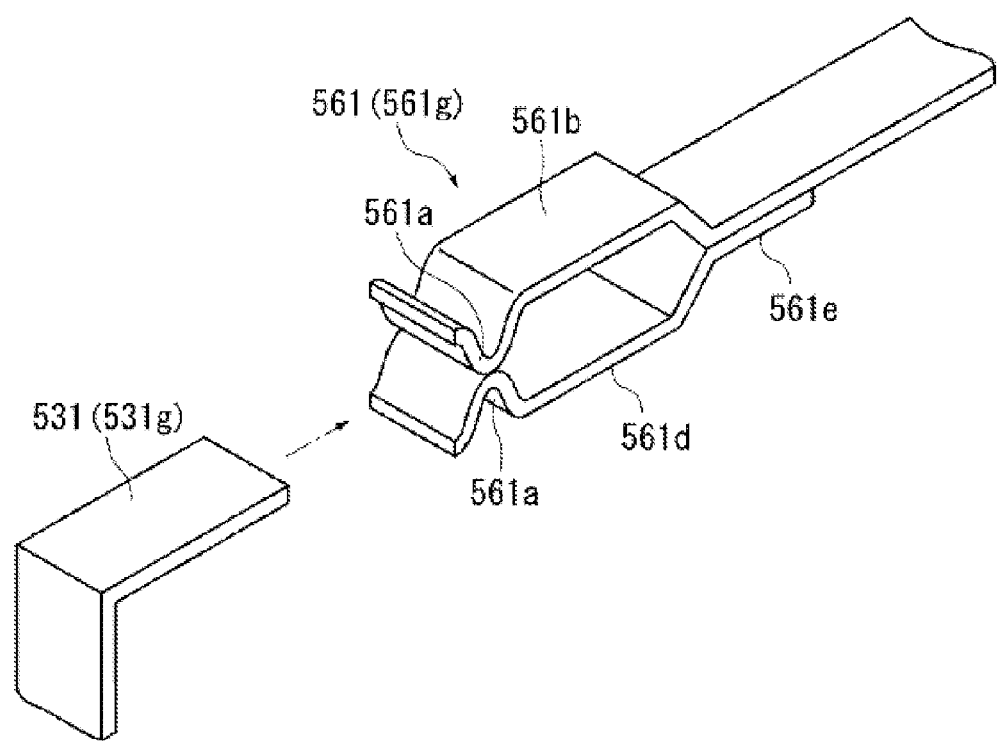
FIG. 13 is a process drawing showing a form of connection between a first connection portion and a second connection portion in the fourth embodiment.

As shown in FIG. 13, the second connection portion 561 assumes the form of a female portion 561g, and the female portion 561g has a main portion 561b connected to the intermediate portion 562 and extending radially and a counter portion 561d, which is a separate member from the main portion 561b, located on the forward side of the main portion 561b, laminated on the main portion 561b in the direction of the axis O, and welded to the main portion 561b to integrate the same. The counter portion 561d is laminated, at its rear end portion 561e, on the main portion 561b, and a portion of the counter portion 561d located on a side toward the axis O with respect to the rear end portion 561e has a shape resembling a crank and extends in parallel with the main portion 561b while being spaced apart in the direction of the axis O from the main portion 561b. Similarly, a portion of the main portion 561b located on a side toward the axis O with respect to the laminate of the main portion 561b and the rear end portion 561e has a shape resembling a crank and is spaced apart in the direction of the axis O from the main portion 561b.

Furthermore, end portions of the main portion 561b and the counter portion 561d are bent in such a manner as to approach each other, to thereby form a pair of elastic portions 561a. In this manner, the female portion 561g of the second connection portion 561 is formed into a clip-like shape, and, by the effect of elastic forces of the main portion 561b and the counter portion 561d, a pair of the elastic portions 561a elastically bends in such a manner as to open and close in the direction of the axis O (a mutually approaching direction).

As shown in FIG. 13, the fourth embodiment differs from the second embodiment in that the insertion piece 531g of the first connection portion 531 is inserted into the connector terminal 560 (the female portion 561g of the second connection portion 561) and that the insertion piece 531g of the first connection portion 531 is held between the paired elastic portions 631a. That is, the insertion piece 531g of the first connection portion 531 can be radially inserted between the paired elastic portions 561a. In the fourth embodiment, the insulator 307 and the body portion 101, to which the insulator 307 is assembled, are similar to those of the second embodiment. Therefore, similar to the second embodiment, in assembling, when the insulator 307 is radially inserted into the connector portion 103 from the opening 104, the cut 307a abuts against the protrusion 101b, whereby the insulator 307 is positioned, and the first connection portion 531 is inserted (fitted) into the second connection portion 561 (the insertion piece 531g is fitted into the female portion 561g) and presses the paired elastic portions 561a, whereby the elastic portions 561a elastically bend in the direction of the axis O. As a result, the first connection portion 531 and the second connection portion 561 are elastically connected. Thus, the connection terminal 530 and the connector terminal 560 can be electrically connected without welding.

In the fourth embodiment, the direction in which the elastic portions 561a elastically bend intersects with a direction of juxtaposition of the first connection portion 531 and the second connection portion 561 (radial direction). Also, the first connection portion 531 is bent radially and is thereby juxtaposed with the second connection portion 561, whereby the first and second connection portions 531 and 561 can be connected.

Next, with reference to FIGS. 14 and 15, the configuration of a gas sensor 600 according to a fifth embodiment of the present invention will be described. The gas sensor 600 is similar to the gas sensor of the first embodiment except that the connection terminals 30 in the first embodiment are replaced with connection terminals 630. Thus, configurational features similar to those of the first embodiment are denoted by like reference numerals, and a detailed description thereof is omitted. Also, the connector terminals 60 are similar to those of the first embodiment.

Figure 14:
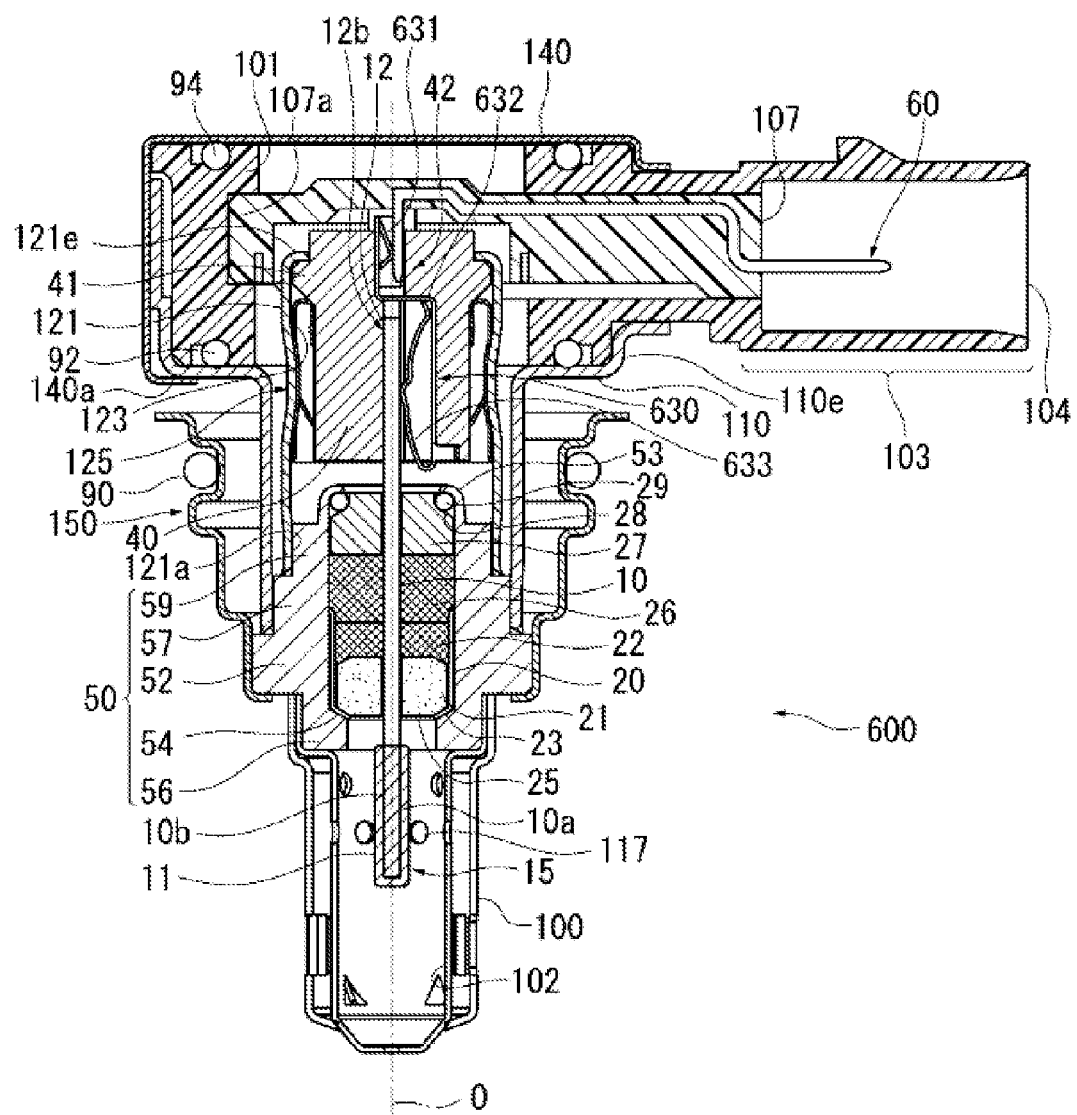
FIG. 14 is a sectional view showing the configuration of a gas sensor according to a fifth embodiment of the invention.

FIG. 14 is a sectional view showing the configuration of the gas sensor 600 and corresponds to FIG. 3 of the first embodiment. In FIG. 14, the connection terminal 630 has a first connection portion 631 extending in the direction of the axis O; a plate-like intermediate portion 632 bent from the first connection portion 631 in a shape of the letter L and extending radially; and a forward portion 633 bent forward from the intermediate portion 632 in a shape of the letter L and extending in the direction of the axis O. The connection terminal 630 is formed into a shape resembling a crank as viewed laterally, and the forward portion 633 is similar to the forward portion 33 of the first embodiment.

Figure 15:
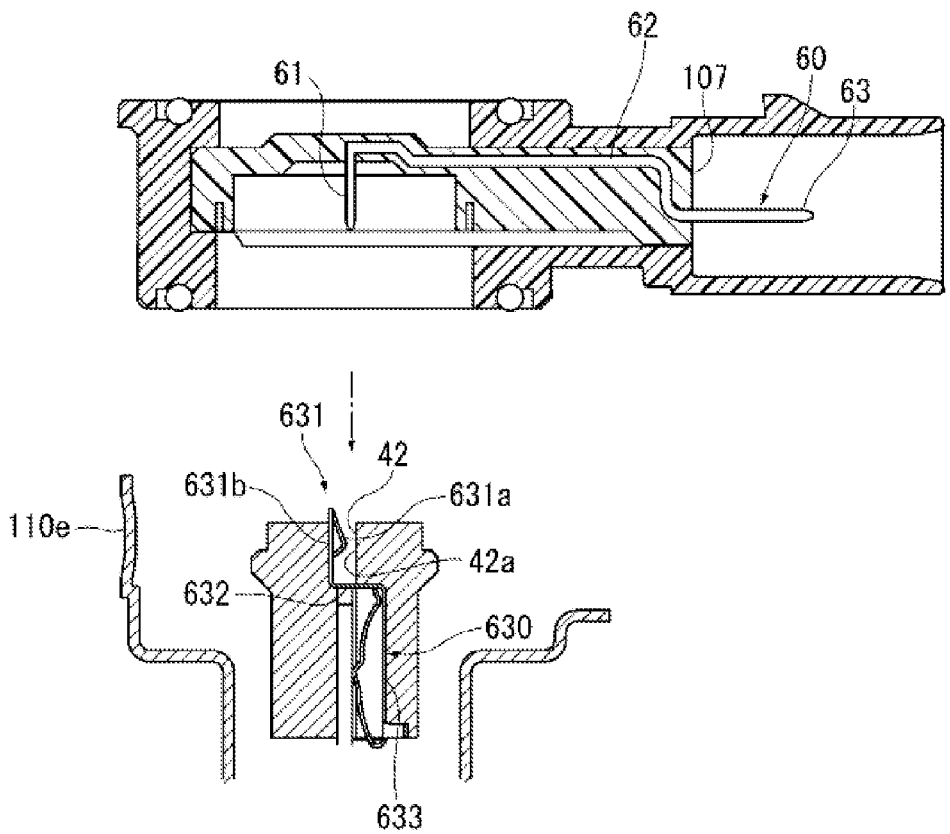
FIG. 15 is a process drawing showing a form of connection between a first connection portion and a second connection portion in the fifth embodiment of the invention.

As shown in FIG. 15, the first connection portion 631 has a main portion 631b connected to the intermediate portion 632 and standing in the direction of the axis O and an elastic portion 631a bent forward from the rearward-oriented surface of the main portion 631b. The elastic portion 631a is located between the main portion 631b and an inner surface 42a of the insertion hole 42 of the separator 40 and elastically bends toward the main portion 631b. In the connection terminal 630, a rear end portion of the first connection portion 631 protrudes rearward from the rearward-oriented surface of the separator 40, and the remaining portion is held within the insertion hole 42 of the separator 40. Also, a surface of the main portion 631b on a side opposite the elastic portion 631a is in contact with the inner surface 42a of the insertion hole 42, whereas a surface of the main portion 631b on a side toward the elastic portion 631a is spaced apart from the inner surface 42a of the insertion hole 42.

Meanwhile, the connector terminals (in this example, five pieces) 60 are similar to those of the first embodiment, and the insulator 107 which holds the connector terminals 60 is similar to that of the first embodiment. The second connection portions 61 of the connector terminals 60 are bent forward in the direction of the axis O in a shape of the letter L.

As shown in FIG. 15, the fifth embodiment differs from the first embodiment in that the second connection portion 61 is held between the elastic portion 631a and the inner surface 42a of the insertion hole 42 of the separator 40. Meanwhile, in the fifth embodiment, the insulator 107 and the body portion 101, to which the insulator 107 is assembled, are similar to those of the first embodiment. Similar to the first embodiment, the trunk member 105 (the body portion 101 thereof) is fitted, from the rear side, into the rear tube 110e to which the separator assembly 120 is assembled (see FIG. 6(d)). At this time, the second connection portion 61 of the connector terminal 60 is inserted between the elastic portion 631a of the first connection portion 631 and the inner surface 42a of the insertion hole 42 and presses the elastic portion 631a while being held against the inner surface 42a. Thus, the elastic portion 631a elastically bends in a radial direction. As a result, the first connection portion 631 and the second connection portion 61 are elastically connected. Further, the connection terminal 630 and the connector terminal 60 can be electrically connected without welding.

The inner surface 42a of the insertion hole 42 of the separator 40 corresponds to "a surface of the separator" of the invention.

In the fifth embodiment, the direction in which the elastic portion 631a elastically bends intersects with a direction of juxtaposition of the first connection portion 631 and the second connection portion 61 (the direction of the axis O). Also, the second connection portion 61 is bent in the direction of the axis O and is thereby juxtaposed with the first connection portion 631, whereby the first and second connection portions 631 and 61 can be connected.

Next, with reference to FIGS. 16 and 17, the configuration of a gas sensor 700 according to a sixth embodiment of the present invention will be described. The gas sensor 700 is similar to the gas sensor of the first embodiment except that the connection terminals 30 and the connector terminals 60 in the first embodiment are replaced with connection terminals 730 and connector terminals 760, respectively. Thus, configurational features similar to those of the first embodiment are denoted by like reference numerals, and detailed description thereof is omitted.

Figure 16:
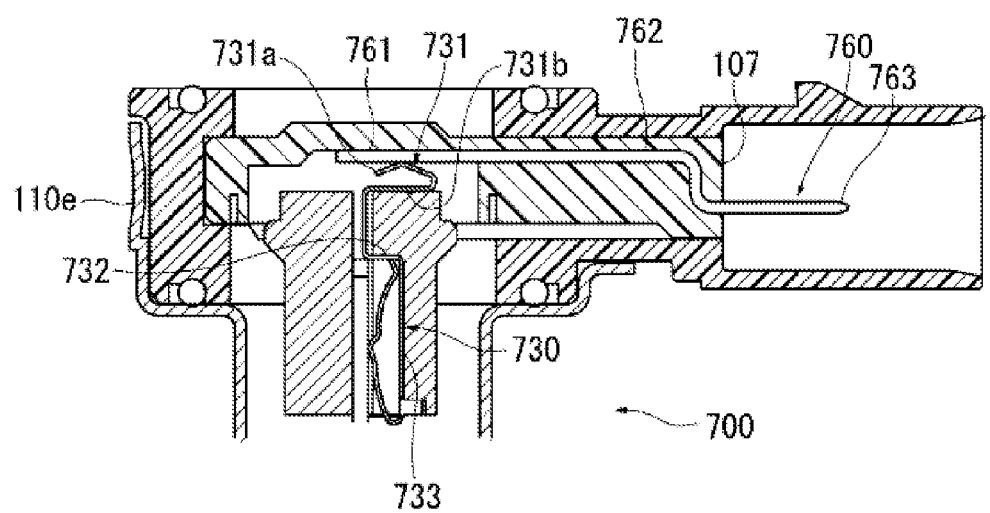
FIG. 16 is a sectional view showing the configuration of a gas sensor according to a sixth embodiment of the invention.

FIG. 16 is a sectional view showing the configuration of the gas sensor 700 and corresponds to FIG. 3 of the first embodiment. In FIG. 16, the connection terminal 730 has a first connection portion 731 extending in the direction of the axis O; a plate-like intermediate portion 732 bent from the first connection portion 731 in a shape of the letter L and extending radially; and a forward portion 733 bent forward from the intermediate portion 732 in a shape of the letter L and extending in the direction of the axis O. The connection terminal 730 is formed into a shape resembling a crank as viewed laterally, and the forward portion 733 is similar to the forward portion 33 of the first embodiment. Also, the first connection portion 731 is bent from the intermediate portion 732 in a shape of the letter L, extends in the direction of the axis O, and has a main portion 731b and an elastic portion 731a formed as follows: a rear end portion of the first connection portion 731 is bent in a shape of the letter L and extends radially so as to form the main portion 731b, and a radially outward end portion of the main portion 731b is bent back in a radially opposite direction so as to form the elastic portion 731a. The elastic portion 731a elastically bends toward the main portion 731b (forward).

In the connection terminal 730, a rear end portion of the first connection portion 731 protrudes rearward from the rearward-oriented surface of the separator 40, and the remaining portion is held within the insertion hole 42 of the separator 40.

Meanwhile, the connector terminals (in this example, five pieces) 760 are similar in configuration to those of the first embodiment except for second connection portions 761, and the insulator 107 which holds the connector terminals 60 is similar to that of the first embodiment. The second connection portions 761 of the connector terminals 760 extend radially in parallel with intermediate portions 762 while being in contact with an inner surface 107a of the insulator 107, and the forward-oriented surfaces (plate surfaces) of the second connection portions 761 are exposed. The connector terminals 760 are insert-molded to the insulator 107, and the rearward-oriented surfaces (plate surfaces) of the second connection portions 761 are fixedly embedded in the resin of the insulator 107.

Figure 17:
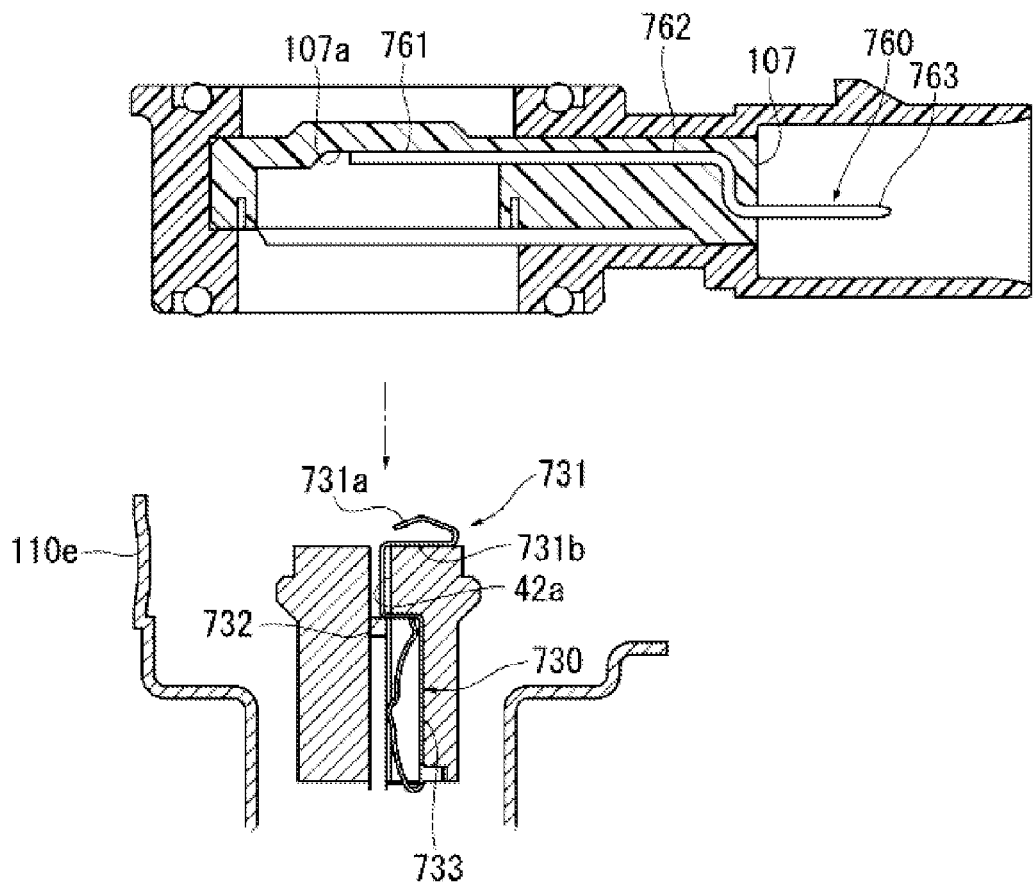
FIG. 17 is a process drawing showing a form of connection between a first connection portion and a second connection portion in the sixth embodiment.

As shown in FIG. 17, the sixth embodiment differs from the first embodiment in that the second connection portion 761 is held between the elastic portion 731a and the inner surface 107a of the insulator 107. In the sixth embodiment, the insulator 107 and the body portion 101, to which the insulator 107 is assembled, are similar to those of the first embodiment. Similar to the first embodiment, the trunk member 105 (the body portion 101 thereof) is fitted, from the rear side, into the rear tube 110e to which the separator assembly 120 is assembled. At this time, the second connection portion 761 of the connector terminal 760 resides on the rear side of the elastic portion 731a of the first connection portion 731 and presses the elastic portion 731a, whereby the elastic portion 731a elastically bends in the direction of the axis O. As a result, the first connection portion 731 and the second connection portion 761 are elastically connected. Thus, the connection terminal 730 and the connector terminal 760 can be electrically connected without welding.

The inner surface 107a of the insulator 107 corresponds to "an inner surface of the trunk member" of the invention.

In the sixth embodiment, the direction in which the elastic portion 731a elastically bends intersects with a direction of juxtaposition of the first connection portion 731 and the second connection portion 761 (radial direction). Also, the first connection portion 731 is bent radially and is thereby juxtaposed with the second connection portion 761, whereby the first and second connection portions 731 and 761 can be connected.

Next, with reference to FIG. 18, the configuration of a gas sensor 800 according to a seventh embodiment of the present invention will be described. The gas sensor 800 is similar to the gas sensor of the first embodiment except that the connection terminals 30, the connector terminals 60, and the insulator 107 in the first embodiment are replaced with connection terminals 830, connector terminals 860, and the insulator 807, respectively. Thus, configurational features similar to those of the first embodiment are denoted by like reference numerals, and a detailed description thereof is omitted.

Figure 18:
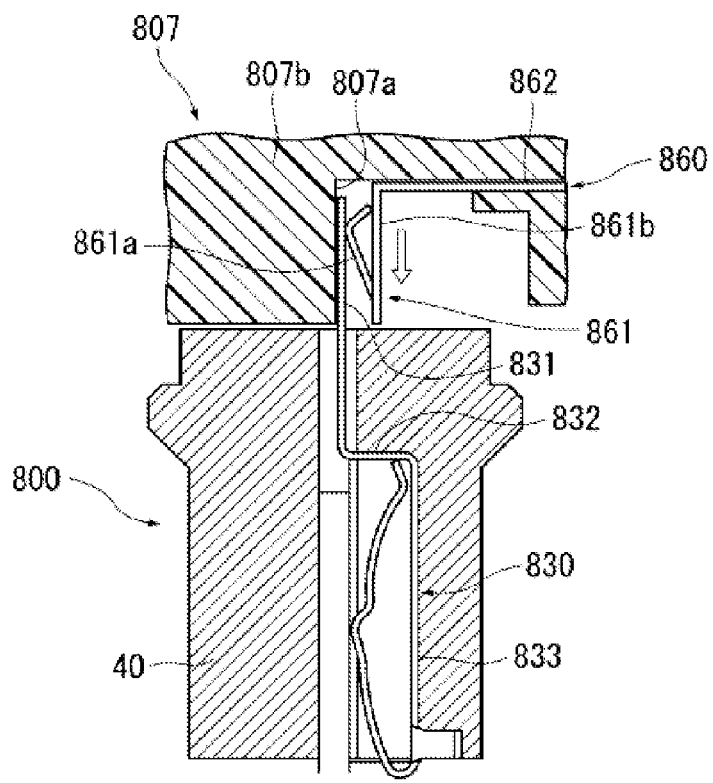
FIG. 18 is a partial, sectional view showing the configuration of a gas sensor according to a seventh embodiment of the invention.

FIG. 18 is a sectional view showing the configuration of the gas sensor 800 and corresponds to FIG. 3 of the first embodiment. FIG. 18 only shows the configuration of the connection terminal 830, the connector terminal 860, and their periphery and omits other configurational features.

The connection terminal 830 has a first connection portion 831 extending in the direction of the axis O; a plate-like intermediate portion 832 bent from the first connection portion 831 in a shape of the letter L and extending radially; and a forward portion 833 bent forward from the intermediate portion 832 in a shape of the letter L and extending in the direction of the axis O. The connection terminal 830 is formed into a shape resembling a crank as viewed laterally, and the forward portion 833 is similar to the forward portion 33 of the first embodiment.

In the connection terminal 830, a rear end portion of the first connection portion 831 protrudes rearward from the rearward-oriented surface of the separator 40, and the remaining portion is held within the insertion hole of the separator 40.

Meanwhile, the connector terminals (in this example, five pieces) 860 are held in the insulator 807 while being separated from one another. Each of the connector terminals 860 has a plate-like intermediate portion 862 extending radially and embedded in the insulator 807; a second connection portion 861 bent from the intermediate portion 862 in a shape of the letter L and extending in the direction of the axis O; and a male portion (not shown) protruding radially outward from the insulator 807. The male portion and the intermediate portion 862 are similar to those of the first embodiment.

The insulator 807 has an overhang portion 807b which overhangs forward at a position located more toward the axis O than the second connection portion 861. A side surface 807*a* of the overhang portion 807*b* extends in parallel with a main surface 861*b* while being spaced apart from the main surface 861*b*. The second connection portion 861 has the main surface 861*b* extending in the direction of the axis O and an elastic portion 861*a* bent rearward from the forward end of the main surface 861*b*. The elastic portion 861*a* faces the overhang portion 807*b* and elastically bends in a direction moving away from the main surface 861*b* (in a direction approaching the overhang portion 807*b*).

The seventh embodiment differs from the first embodiment in that the first connection portion 831 is held between the elastic portion 861*a* of the second connection portion 861 and the side surface 807*a* of the insulator 807. Meanwhile, in the seventh embodiment, the body portion 101 to which the insulator 807 is assembled is similar to that of the first embodiment. Similar to the first embodiment, the trunk member 105 (the body portion 101 thereof) is fitted, from the rear side, into the rear tube 110*e* to which the separator assembly 120 is assembled. At this time, the first connection portion 831 is inserted (fitted) in the direction of the axis O (see the arrow in FIG. 18) between the second connection portion 861 and the side surface 807*a* of the insulator 807 and thereby presses the elastic portion 861*a*, whereby the elastic portion 861*a* elastically bends in the direction of the axis O. As a result, the first connection portion 831 and the second connection portion 861 are elastically connected. Thus, the connection terminal 830 and the connector terminal 860 can be electrically connected without welding.

The side surface 807*a* of the insulator 807 corresponds to "an inner surface of the trunk member" of the invention.

In the seventh embodiment, the direction in which the elastic portion 861*a* elastically bends intersects with a direction of juxtaposition of the first connection portion 831 and the second connection portion 861 (the direction of the axis O). Also, the second connection portion 861 is bent in the direction of the axis O and is thereby juxtaposed with the first connection portion 831, whereby the first and second connection portions 831 and 861 can be connected.

Next, with reference to FIG. 19, the configuration of a gas sensor 900 according to an eighth embodiment of the present invention will be described. The gas sensor 900 is similar to the gas sensor of the second embodiment except that the connection terminals 30 and the connector terminals 60 in the first embodiment are replaced with connection terminals 930 and connector terminals 960, respectively. Thus, configurational features similar to those of the second embodiment are denoted by like reference numerals, and a detailed description thereof is omitted.

Figure 19:
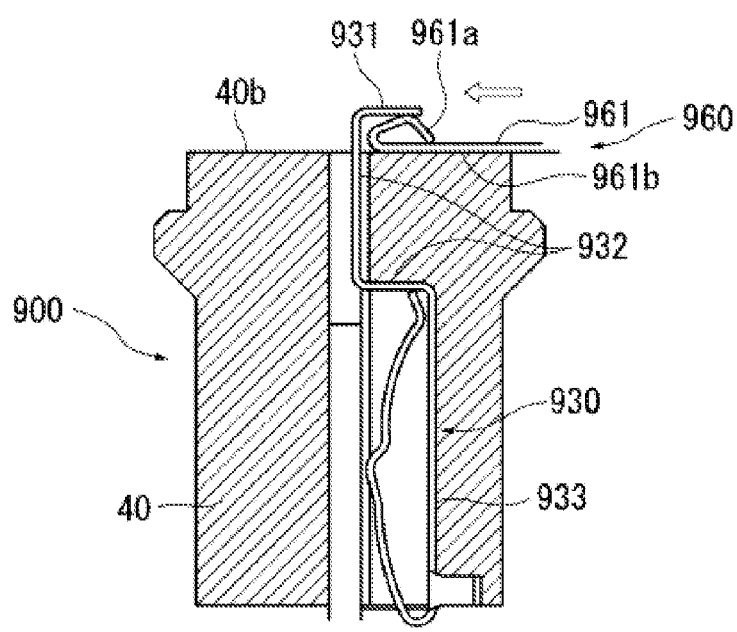
FIG. 19 is a partial, sectional view showing the configuration of a gas sensor according to an eighth embodiment of the invention.

FIG. 19 is a sectional view showing the configuration of the gas sensor 900 and corresponds to FIG. 8 of the second embodiment. FIG. 19 only shows the configuration of the connection terminal 930, the connector terminal 960, and their periphery and omits other configurational features.

The connection terminal 930 has a first connection portion 931 extending in the direction of the axis O; a plate-like intermediate portion 932 bent from the first connection portion 931 in a shape of the letter L and extending radially; and a forward portion 933 bent forward from the intermediate portion 932 in a shape of the letter L and extending in the direction of the axis O. The connection terminal 930 is formed into a shape resembling a crank as viewed laterally, and the forward portion 933 is similar to the forward portion 333 of the second embodiment.

As shown in FIG. 19, the first connection portion 931 is bent from the intermediate portion 932 in a shape of the letter L; extends in the direction of the axis O; and is bent at its rear end portion in a shape of the letter L and extends radially. In the connection terminal 930, the first connection portion 931 protrudes rearward from the rearward-oriented surface of the separator 40, and the remaining portion is held within the insertion hole of the separator 40. Furthermore, the gap between the first connection portion 931 and the rearward-oriented surface 40*b* of the separator 40 is narrower than the height along the direction of the axis O from a main portion 961*b* of the connector terminal 960 to an elastic portion 961*a*.

Meanwhile, the connector terminals (in this example, five pieces) 960 are held in an insulator (not shown) while being separated from one another. Each of the connector terminals 960 has a plate-like intermediate portion (not shown) extending radially and embedded in the insulator (not shown); a second connection portion 961, which is an end portion protruding from the intermediate portion toward the separator 40, extending radially; and a male portion (not shown) protruding radially outward from the insulator.

The second connection portion 961 has the main portion 961*b* extending radially and connected to the intermediate portion, and the elastic portion 961*a* bent back from an end portion of the main portion 961*b* toward the intermediate portion. The elastic portion 961*a* elastically bends in a direction moving away from the main surface 961*b* (i.e., rearward).

The eighth embodiment differs from the second embodiment in that the second connection portion 961 is inserted (fitted) between the first connection portion 931 and the rearward-oriented surface 40*b* of the separator 40. Meanwhile, in the eighth embodiment, similar to the second embodiment, the body portion 101 (the trunk member 105) in a state before attachment of the insulator thereto is fitted into the rear tube 110*e* to which the separator assembly 120 is assembled. Subsequently, the insulator 307 is radially inserted into the connector portion 103 from the opening 104. At this time, the second connection portion 961 is radially inserted (fitted) (see the arrow in FIG. 19) between the first connection portion 931 and the rearward-oriented surface 40*b* of the separator 40; accordingly, the forward-oriented surface of the first connection portion 931 presses the elastic portion 961*a* of the second connection portion 961, whereby the elastic portion 961*a* elastically bends in the direction of the axis O. As a result, the first connection portion 931 and the second connection portion 961 are elastically connected; thus, the connection terminal 930 and the connector terminal 960 can be electrically connected without employment of welding.

The rearward-oriented surface 40*b* of the separator 40 corresponds to "a surface of the separator" of the invention.

In the eighth embodiment, the direction in which the elastic portion 961*a* elastically bends intersects with a direction of juxtaposition of the first connection portion 931 and the second connection portion 961 (radial direction). Also, the first connection portion 931 is bent radially and is thereby juxtaposed with the second connection portion 961, whereby the first and second connection portions 931 and 961 can be connected.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

For example, instead of bending one of the first connection portion and the second connection portion for juxtaposing these members with one another, both of the first connection portion and the second connection portion may be bent (for example, both may be bent in a direction forming an angle of 45 degrees with the direction of the axis) and juxtaposed with one another.

This application is based on Japanese Patent Application No. 2012-160436 filed Jul. 19, 2012 and Japanese Patent Application No. 2013-090089 filed Apr. 23, 2013, the above-noted applications incorporated herein by reference in their entirety.

What is claimed is:

1. A gas sensor comprising:
a gas sensor element extending in a direction of an axis, the gas sensor element having a detection portion provided at a forward end thereof for detecting a particular gas component in a gas to be measured, the gas sensor element is an elongated plate-shaped element having an outer surface, and the gas sensor element having an electrode pad on the outer surface provided at a rear end portion thereof;
a metallic shell surrounding a radial circumference of the gas sensor element and holding the gas sensor element therein;
an electrically insulating separator having a rear end portion of the gas sensor element disposed within an insertion hole thereof;
a connection terminal which is inserted into the insertion hole and whose forward portion extends in the direction of the axis and is electrically connected to the electrode pad;
a trunk member having a body portion surrounding the separator, and a connector portion extending from the body portion in a radial direction intersecting the direction of the axis and configured to allow an external device to be inserted thereinto and removed therefrom; and
a connector terminal held in the connector portion and extending through the connector portion in a radial direction intersecting the direction of the axis; wherein
the connection terminal has, at a rear end portion, a first connection portion electrically connected to the connector terminal, and the connection terminal has, at an end portion on a side toward the separator, a second connection portion electrically connected to the first connection portion;
one or both of the first connection portion and the second connection portion is bent such that the first connection portion and the second connection portion are juxtaposed with one another;
one of the first connection portion and the second connection portion assumes the form of an insertion piece, the other one assumes the form of a female portion into which the insertion piece is inserted, and at least one of the insertion piece and the female portion has an elastic portion elastically bendable in a direction intersecting a direction of juxtaposition of the first connection portion and the second connection portion; and
the insertion piece is fitted into the female portion such that the elastic portion elastically bends in the intersecting direction, whereby the first connection portion and the second connection portion are elastically connected.

2. The gas sensor as claimed in claim 1, wherein the second connection portion assumes the form of the insertion piece, and the first connection portion assumes the form of the female portion.

3. The gas sensor as claimed in claim 2, wherein
the second connection portion is bent, and the insertion piece extends in the direction of the axis, and
the female portion of the first connection portion is located within the insertion hole.

4. A gas sensor comprising:
a gas sensor element extending in a direction of an axis, the gas sensor element having a detection portion provided at a forward end thereof for detecting a particular gas component in a gas to be measured, the gas sensor element is an elongated plate-like element having an outer surface, and the gas sensor element having an electrode pad on the outer surface provided at a rear end portion thereof;
a metallic shell surrounding a radial circumference of the gas sensor element and holding the gas sensor element therein;
an electrically insulating separator having a rear end portion of the gas sensor element disposed within an insertion hole thereof;
a connection terminal which is inserted into the insertion hole and extends in the direction of the axis and whose forward portion is electrically connected to the electrode pad;
a trunk member formed of an electrically insulating material, having a body portion surrounding the separator, and a connector portion extending from the body portion in a direction intersecting the direction of the axis and configured to allow an external device to be inserted thereinto and removed therefrom; and
a connector terminal held in the connector portion and extending through the connector portion in a direction intersecting with the direction of the axis; wherein
the connection terminal has, at a rear end portion, a first connection portion electrically connected to the connector terminal, and the connection terminal has, at an end portion on a side toward the separator, a second connection portion electrically connected to the first connection portion;
one or both of the first connection portion and the second connection portion is bent such that the first connection portion and the second connection portion are juxtaposed with one another;
at least one of the first connection portion and the second connection portion has an elastic portion elastically bendable in a direction intersecting a direction of extension of the first connection portion and the second connection portion; and
one connection portion of the first and second connection portions is sandwiched between a surface of the separator or an inner surface of the trunk member and the other connection portion, such that the elastic portion elastically bends in the intersecting direction, whereby the first connection portion and the second connection portion are elastically connected.

5. The gas sensor as claimed in claim 4, wherein the second connection portion is the one connection portion, and the first connection portion is the other connection portion.

6. The gas sensor as claimed in claim 5, wherein
the second connection portion is bent and extends in the direction of the axis, and
the second connection portion is disposed between an inner surface of the insertion hole of the separator and the first connection portion.

7. The gas sensor as claimed in claim 1, wherein the connection terminal is formed of a material having a heat resistance higher than that of a material used to form the connector terminal.

8. The gas sensor as claimed in claim 1, wherein the connector terminal is formed of a copper-based material, and the connection terminal is formed of stainless steel or a Ni-based alloy.

9. The gas sensor as claimed in claim 1, wherein the trunk member further comprises an insulator which is accommodated in the body portion of the trunk member and in which a portion of the connector terminal is embedded.

10. The gas sensor as claimed in claim 1, wherein plural connection terminals are held in the separator.

11. The gas sensor as claimed in claim 1, wherein plural connector terminals are held in the trunk member.

12. The gas sensor as claimed in claim 1, wherein the elastic portion is a spring portion having a free end.

13. The gas sensor as claimed in claim 4, wherein the connection terminal is formed of a material having a heat resistance higher than that of a material used to form the connector terminal.

14. The gas sensor as claimed in claim 4, wherein the connector terminal is formed of a copper-based material, and the connection terminal is formed of stainless steel or a Ni-based alloy.

15. The gas sensor as claimed in claim 4, wherein the trunk member further comprises an insulator which is accommodated in the body portion of the trunk member and in which a portion of the connector terminal is embedded.

16. The gas sensor as claimed in claim 4, wherein plural connection terminals are held in the separator.

17. The gas sensor as claimed in claim 4, wherein plural connector terminals are held in the trunk member.

18. The gas sensor claimed in claim 4, wherein the elastic portion is a spring portion having a free end.

\* \* \* \* \*